(12) United States Patent
Hulvershorn et al.

(10) Patent No.: US 12,059,248 B2
(45) Date of Patent: Aug. 13, 2024

(54) QUANTITATIVE NEUROMUSCULATURE BLOCKADE SENSING SYSTEMS AND METHODS

(71) Applicant: BLINK DEVICE LLC, Seattle, WA (US)

(72) Inventors: Justin Hulvershorn, Seattle, WA (US); Karl Schmidt, Seattle, WA (US); Tyler Hart, Seattle, WA (US)

(73) Assignee: Blink Device LLC, Seattle, WA (US)

( * ) Notice: Subject to any disclaimer, the term of this patent is extended or adjusted under 35 U.S.C. 154(b) by 1158 days.

(21) Appl. No.: 16/339,163

(22) PCT Filed: Oct. 13, 2017

(86) PCT No.: PCT/US2017/056653
§ 371 (c)(1),
(2) Date: Apr. 3, 2019

(87) PCT Pub. No.: WO2018/071860
PCT Pub. Date: Apr. 19, 2018

(65) Prior Publication Data
US 2019/0223764 A1     Jul. 25, 2019

Related U.S. Application Data

(60) Provisional application No. 62/469,310, filed on Mar. 9, 2017, provisional application No. 62/408,327, filed on Oct. 14, 2016.

(51) Int. Cl.
*A61B 5/05* (2021.01)
*A61B 5/00* (2006.01)
(Continued)

(52) U.S. Cl.
CPC .............. *A61B 5/1106* (2013.01); *A61B 5/24* (2021.01); *A61B 5/296* (2021.01); *A61B 5/305* (2021.01);
(Continued)

(58) Field of Classification Search
CPC ......... A61B 5/1106; A61B 5/296; A61B 5/24; A61B 5/389; A61B 5/6826; A61B 5/6833; A61B 5/7217; A61B 5/685; A61B 5/257
(Continued)

(56) References Cited

U.S. PATENT DOCUMENTS 4,387,723 A    6/1983  Atlee, III et al.
5,542,729 A    8/1996  Ohtonen
(Continued)

FOREIGN PATENT DOCUMENTS

CN    1859870 A    11/2006
EP    0993270 A1    4/2000
(Continued)

OTHER PUBLICATIONS

Chinese Office Action dated Jul. 7, 2021 in counterpart Chinese Patent Application No. 201780077122.2 (17 pages, in Chinese with English translation).
(Continued)

*Primary Examiner* — Joseph A Stoklosa
*Assistant Examiner* — Brian M Antiskay
(74) *Attorney, Agent, or Firm* — Bookoff McAndrews, PLLC

(57) ABSTRACT

Neuromuscular monitoring is described that uses a novel lead assembly and a monitor that can select the appropriate electrodes on the lead assembly and calibrate the stimulation signals applied to the patient through the lead assembly. The monitoring can also set a noise floor value to reduce the
(Continued)

likelihood of an erroneous train of four calculations. The present system can automatically sense train of four response of a patient and reduce the likelihood of false train of four indications.

24 Claims, 18 Drawing Sheets

(51) Int. Cl.
| | |
|---|---|
| A61B 5/11 | (2006.01) |
| A61B 5/24 | (2021.01) |
| A61B 5/296 | (2021.01) |
| A61B 5/305 | (2021.01) |
| A61B 5/388 | (2021.01) |
| A61B 5/389 | (2021.01) |
| A61B 5/395 | (2021.01) |
| A61N 1/00 | (2006.01) |
| A61B 5/294 | (2021.01) |
| A61N 1/04 | (2006.01) |
| G16H 10/60 | (2018.01) |
| G16H 50/20 | (2018.01) |

(52) U.S. Cl.
CPC .............. *A61B 5/388* (2021.01); *A61B 5/389* (2021.01); *A61B 5/395* (2021.01); *A61B 5/6824* (2013.01); *A61B 5/6826* (2013.01); *A61B 5/6833* (2013.01); *A61B 5/685* (2013.01); *A61B 5/7217* (2013.01); *A61B 5/294* (2021.01); *A61B 2560/0238* (2013.01); *A61B 2562/0219* (2013.01); *A61N 1/0456* (2013.01); *G16H 10/60* (2018.01); *G16H 50/20* (2018.01)

(58) Field of Classification Search
USPC ......... 600/372, 382–393; 607/108, 111–112, 607/115, 118
See application file for complete search history.

(56) References Cited

U.S. PATENT DOCUMENTS

| | | | |
|---|---|---|---|
| 5,851,191 A | 12/1998 | Gozani | |
| 6,389,312 B1 | 5/2002 | Duckert | |
| 6,984,207 B1 | 1/2006 | Sullivan et al. | |
| 7,058,438 B2 | 6/2006 | Grace et al. | |
| 7,308,317 B1 | 12/2007 | Okandan et al. | |
| 7,628,761 B2 | 12/2009 | Gozani et al. | |
| 8,983,613 B2 | 3/2015 | Kamataki et al. | |
| 9,814,402 B2 | 11/2017 | Gadsby | |
| 2001/0000526 A1 | 4/2001 | Gopinathan et al. | |
| 2003/0009096 A1* | 1/2003 | Lahteenmaki | A61B 5/30 600/383 |
| 2006/0270943 A1 | 11/2006 | Kamataki et al. | |
| 2008/0051673 A1 | 2/2008 | Kong et al. | |
| 2010/0081963 A1 | 4/2010 | Gilhuly | |
| 2011/0295096 A1 | 12/2011 | Bibian et al. | |
| 2012/0172682 A1* | 7/2012 | Linderman | A61B 5/389 600/300 |
| 2013/0204155 A1* | 8/2013 | Brull | A61B 5/4848 600/546 |
| 2013/0204156 A1 | 8/2013 | Hampton et al. | |
| 2014/0012157 A1 | 1/2014 | Gilhuly | |
| 2014/0088394 A1* | 3/2014 | Sunderland | A61B 5/303 600/373 |
| 2014/0107524 A1 | 4/2014 | Brull et al. | |
| 2014/0207017 A1* | 7/2014 | Gilmore | A61B 5/389 600/546 |
| 2014/0235991 A1 | 8/2014 | Gadsby | |
| 2014/0303471 A1* | 10/2014 | Rajaraman | A61B 5/24 607/148 |
| 2015/0051506 A1 | 2/2015 | Wybo et al. | |
| 2015/0366480 A1 | 12/2015 | Eger et al. | |
| 2016/0313801 A1 | 10/2016 | Wagner et al. | |
| 2018/0199846 A1* | 7/2018 | Eger | A61B 5/296 |
| 2019/0008453 A1 | 1/2019 | Spoof | |
| 2019/0059808 A1 | 2/2019 | Ukawa et al. | |
| 2020/0245883 A1* | 8/2020 | Lucci | A61B 5/0022 |

FOREIGN PATENT DOCUMENTS

| | | |
|---|---|---|
| JP | 2013-121369 A | 6/2013 |
| JP | 2014-133123 A | 7/2014 |
| JP | 2015-506245 A | 3/2015 |
| JP | 2015-506246 A | 3/2015 |
| JP | 2016-508400 A | 3/2016 |
| WO | 2008031209 A1 | 3/2008 |
| WO | 2013/172830 A1 | 11/2013 |
| WO | 2015/097174 A2 | 7/2015 |

OTHER PUBLICATIONS

Biro et al. "Proposal for a Revised Classification of the Depth of Neuromuscular Block and Suggestions for Further Development in Neuromuscular Monitoring," Anesthesia & Analgesia, International Anesthesia Research Society, 2019 (3 pages).
Justin W. Hulvershorn, MD, PhD "Toward an Ideal Neuromuscular Monitor," Letters to the Editor, Anesthesia & Analgesia, International Anesthesia Research Society, May 13, 2019 (2 pages).
First Search Report dated Jul. 7, 2021, in counterpart Chinese Patent Application No. 201780077122.2 (2 pages).
International Search Report dated Apr. 13, 2018 for corresponding International Application PCT/US2017/056653.
I. Kalli "Effect of Surface Electrode Position on the Compound Action Potential Evoked by Ulnar Nerve Stimulation during Isoflurane Anaesthesia" British Journal of Anaesthesia 1990; 65; 494-499.
Japanese Office Action dated Sep. 1, 2020, in counterpart Japanese Patent Application No. 2019-519379 (3 pages in Japanese, and 4 pages with English translation).
Korean Office Action dated Feb. 11, 2022, in counterpart Korean Patent Application No. 10-2019-7013812 (19 pages, in Korean with English translation).
Japanese Office Action dated Apr. 5, 2022, in counterpart Japanese Patent Application No. 2021-112512 (9 pages, in Japanese with English translation).
Search Report issued in corresponding European Patent Application No. 23187035.3, dated Oct. 4, 2023 (5 pages).

\* cited by examiner

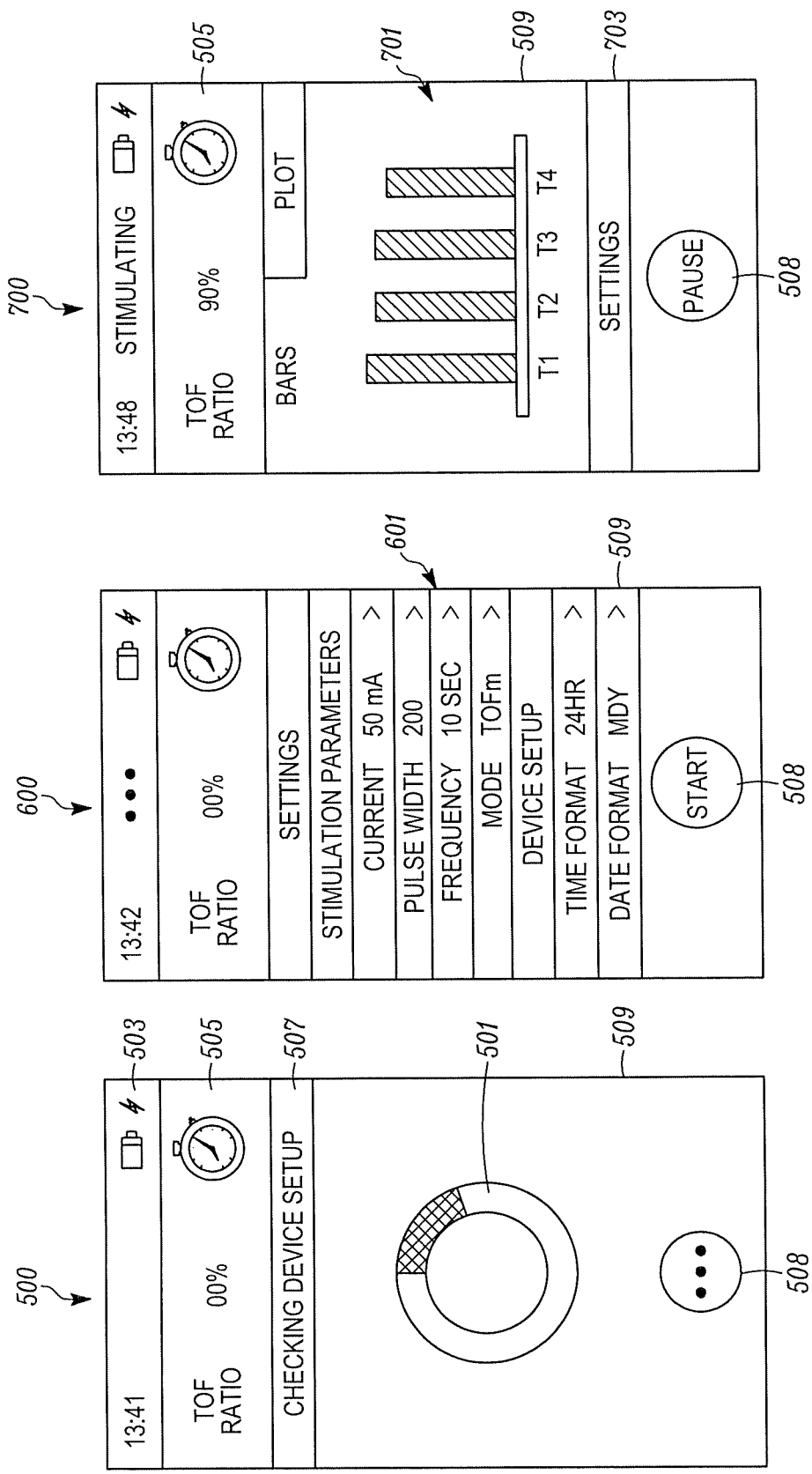

QUANTITATIVE NEUROMUSCULATURE BLOCKADE SENSING SYSTEMS AND METHODS

CROSS-REFERENCE TO RELATED APPLICATIONS

This application is a U.S. National Stage of International Application No. PCT/US2017/056653, filed Oct. 13, 2017, which claims the benefit and priority of U.S. Provisional Application No. 62/469,310, filed Mar. 9, 2017, and of U.S. Provisional Application No. 62/408,327, filed Oct. 14, 2016. The entire disclosures of each of the above applications are incorporated herein by reference.

TECHNICAL FIELD

System and methods for neuromuscular block detection are described.

BACKGROUND

Two key pharmaceutical components of modern general anesthesia include (1) the anesthetic drugs responsible for unconsciousness, and (2) the neuromuscular blocking drugs that cause muscle paralysis. It is not uncommon for patients to wake up partially paralyzed (residual neuromuscular blockade), which can lead to significant patient harm (e.g. impaired respiratory ability).

There are at least three methods to assess the degree of neuromuscular blockade. The simplest and least precise is to ask the patient to move, like lifting his head off the bed for a given number of seconds. This test is quite variable, and, more importantly, requires an awake, responsive patient. It is more desirable to have a test that can be done when the patient is still unconscious, such that when the patient wakes up, the anesthesiologist can be assured that they will have adequate motor function. In the anesthetized (unconscious) patient, a nerve can be electrically stimulated, resulting in movement of the innervated muscle. For example, stimulation of the ulnar nerve near the wrist causes the thumb and index finger to contract. The anesthesiologist can watch or feel the thumb during this electrical stimulation to see if the thumb moves in response to an electrical stimulus. This type of monitoring is often referred to as peripheral nerve stimulation, or qualitative (or non-quantitative) neuromuscular monitoring. A third and more sophisticated method involves the addition of a movement detection element to the peripheral nerve stimulator as described above. These devices are referred to as quantitative neuromuscular monitors, or quantitative twitch monitors, as the movement is detected not by the doctor's thumb, but rather by some detection device, for example, one based on accelerometry or electromyography. The advantage of these types of devices is a more precise quantification of the degree of movement, which can give the anesthesiologist a better idea of the degree of paralysis.

SUMMARY

A neuromuscular lead assembly for neuromuscular blockade monitoring is described and may include a base supporting a plurality of electrodes. A first plurality of electrodes is mechanically supported by the base and configured to be connected to a patient for stimulation. A second plurality of electrodes is supported by the base and in electrical communication with the patient for sensing a response to the stimulation signal. The second plurality of electrodes is configured to electrically communicate with a processor to detect muscle activity in response to a stimulation signal from at least one of the first plurality of stimulation electrodes. The second plurality of sensing electrodes is configured to be selectable with at least one of the plurality of sensing electrodes not detecting patient movement.

The base of the lead assembly may be nonlinear so as to position the second plurality of sensing electrodes at anatomically desired positions on a hand of the patient and the first plurality of stimulation electrodes at anatomically desired positions on a forearm of the patient.

In an example embodiment, one electrode of the second plurality of sensing electrodes is selected as the optimal detection electrode based on an analysis of the detected signal, with the nonoptimal sensing electrode being used as the driven electrode. The driven electrode may operate to remove common mode signals, which are common to other electrodes connected to the patient.

In an example embodiment, the base, the stimulation electrodes and the sensing electrodes are disposable.

In an example embodiment, the base includes medical grade adhesive to fix the sensing electrodes to the patient for sensing electrical activity.

In an example embodiment, the base includes a first part supporting the first plurality of stimulation electrodes and a second part supporting the second plurality of sensing electrodes. The first part may be separate from the second part. A first plurality of electrical conductors is in electrical communication with the plurality of stimulation electrodes and extends from the first part. A second plurality of electrical conductors is in electrical communication with the plurality of sensing electrodes and extends from the second part. In an example, embodiment, the first plurality of electrical conductors and the second plurality of electrical conductors are mechanically joined remote from the second part.

In an example embodiment, the base encloses the first and second pluralities of conductors.

In an example embodiment, the base includes a thumb aperture to secure the base around a thumb of a patient to position a first sensing electrode on a palm of the patient and a second sensing electrode on a back of a hand of the patient.

In an example embodiment, the second plurality of sensing electrodes further includes a driven electrode. One of the first sensing electrode and the second sensing electrode is selected to sense muscle activity of the patient in response to a stimulation signal and the other of the first sensing electrode and the second sensing electrode is selected as the driven electrode.

A neuromuscular lead assembly for neuromuscular blockade monitoring may include a body, a plurality of electrodes mechanically supported by the body, an accelerometer, a plurality of conductors supported by the body and in electrical communication with the plurality of electrodes, respectively, and wherein the plurality of conductors are configured to electrically communicate with a processor to detect movement in response to stimulation.

In an example embodiment, the body is nonlinear to position the plurality of electrodes at anatomically desired positions on the forearm and hand of a patient.

In an example embodiment, the body, the electrodes and the conductors are disposable.

In an example embodiment, the body includes medical grade adhesive to fix the electrodes to the patient for sensing electrical activity.

In an example embodiment, a stimulation electrode of the plurality of electrodes is to apply a stimulation signal to the patient.

In an example embodiment, a sensing electrode of the plurality of electrodes is to sense a patient response to the stimulation signal applied by the stimulation electrode.

In an example embodiment, the plurality of electrodes includes more than one sensing electrode configured to sense a patient response to the stimulation signal applied by the stimulation electrode.

In an example embodiment, the body encloses the plurality of conductors.

A method of calibrating a neuromuscular monitor on a paralyzed patient is also described and may include starting calibration at a first stimulation signal value; applying successive input signals at the first stimulation signal value for a train of four analysis; measuring a patient train of four response for a T1 response and a train of four ratio; if the train of four ratio is constant and the T1 response increases, then increasing the stimulation value by a increment value to an increased stimulation value; applying successive input signals at the increased stimulation signal value and repeating the measuring and increasing the stimulation value steps; and if the initial patient response to the train of four at the increased stimulation signal value is not constant (i.e. if the train of four ratio changes during application of the successive input signals), then stop the calibration. Additionally, if the T1 response does not increase, then set a calibrated stimulation value to the current stimulation value.

In an example embodiment, the method further includes setting a neuromuscular monitor stimulation value to the calibrated stimulation value increased by a factor.

In an example embodiment, the first stimulation value is 25 mA.

In an example embodiment, the measuring an initial patient response at successive input signals includes measuring a first (T1) height of two successive TOF signals spaced at fifteen second intervals.

In an example embodiment, the increasing the stimulation value by the increment value includes checking a TOF ratio to be the same as the TOF ratio at the prior stimulation value.

In an example embodiment, the factor to set the maximum stimulation value is 1.1.

In an example embodiment, the measuring includes measuring an electrical noise value and using the measured noise to set a current stimulation value.

In an example embodiment, the TOF stimulation value is set to have at least a signal to noise ratio of 1.4 or greater.

In an example embodiment, the TOF stimulation value is set to have at least a signal to noise ratio of 2.0 or greater.

In an example embodiment, the measuring includes applying a zero current stimulation signal for a same time period as the $T_1$ signal.

In an example embodiment, the measuring includes measuring an electrical noise value and using the measured noise to allow or stop use of sensed responses to excitation signals when the sensed patient response approaches, equal to or less than the noise value for the patient connected to the present system.

BRIEF DESCRIPTION OF THE DRAWINGS

FIG. 5 shows a schematic view of a control unit for a neuromuscular monitoring system according to an example embodiment.

FIG. 6 shows a schematic view of a control unit for a neuromuscular monitoring system according to an example embodiment.

FIG. 7 shows a schematic view of a control unit for a neuromuscular monitoring system according to an example embodiment.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Two key pharmaceutical components of modern general anesthesia are (1) the anesthetic drug(s), responsible for unconsciousness, and (2) the neuromuscular blocking drug(s), which cause paralysis in the patient. While new, sophisticated EEG monitors exist to monitor the level of consciousness, the tools for monitoring the level of paralysis (e.g., neuromuscular blockade) are less sophisticated. With advances in anesthesia, in particular, rapidly reversing anesthetics, it is becoming more common for patients to wake up partially paralyzed, e.g., with residual neuromuscular blockade. A patient may experience significant discomfort when, upon waking up from a major operation, the patient finds it difficult to swallow and/or breathe. The presently described systems and methods provide improved tools for monitoring the level of paralysis, e.g., neuromuscular blockade. The presently described systems and methods operate to stimulate a peripheral nerve and measures the resulting electromyographic (EMG) response. Embodiments may provide for a noise floor to filter sensed electrical signal results from the patient to reduce the likelihood of errors in sensing the patient status.

Figure 1:
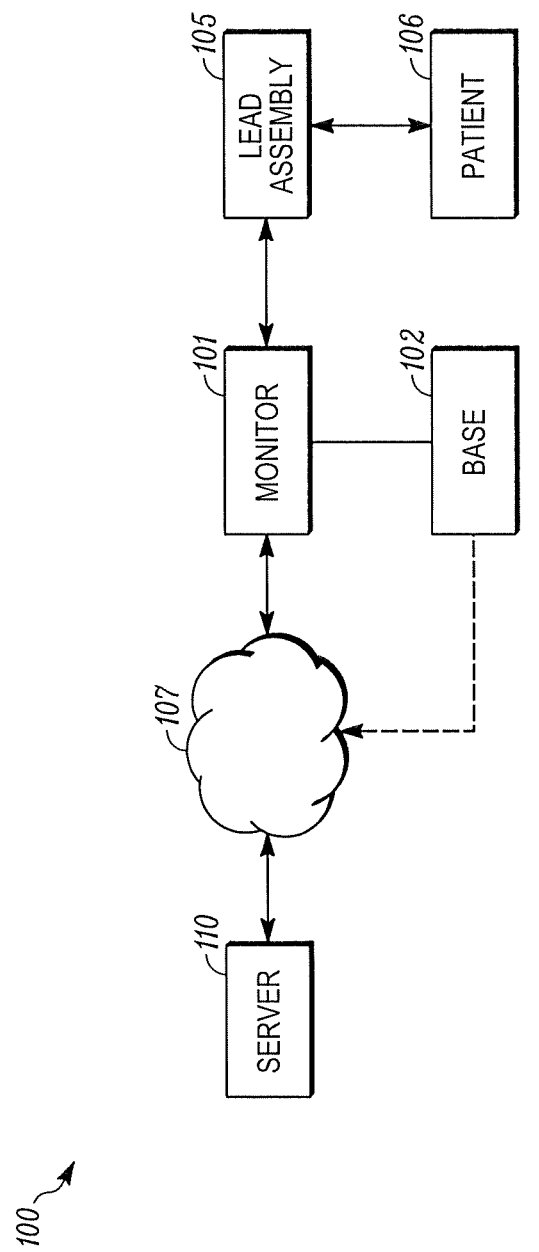
FIG. 1 shows a view of a neuromuscular monitoring system according to an example embodiment.

FIG. 1 shows a monitoring system 100 for quantitative twitch monitoring of a patient. The system 100 can be used to measure the depth of neuromuscular blockade during anesthesia or as a result of anesthesia. A monitor 101 is provided with a base 102. The base 102 can be used to charge the monitor 101 or otherwise provide electrical energy to the monitor 101. The monitor 101 is manufactured to be usable in the sterile environment of operating suites. In an example, the monitor is cleanable to be placed in a surgical suite or surgical room, e.g., with other anesthesia equipment. The base 102, in some embodiments, is also manufactured to be usable in the sterile environment of operating suites. The base 102 may be outside the operating suite and the monitor 101 can be removed from the base 102 and taken into the operating suite. A lead assembly 105 is connected to the monitor 101 and can provide at least sensing functions, with the sensed signals or data being sent to the monitor 101. The lead assembly 105 is configured to be positioned on the patient 106 to detect movement in response to stimulation. The monitor 101 can output a stimulation signal to the lead assembly 105, which in turn senses the response of the patient 106. In an example embodiment, the lead assembly 105 is a single use item that is disposed of after use.

The monitor 101 which includes displays, circuitry, memory and processors, is reusable. The monitor 101 may include a housing, which can be an injection molded case, in which are enclosed a rechargeable battery, charging circuitry, stimulation circuitry, a display (e.g., a touchscreen LCD), display circuitry, and processor board with processor(s) and a memory. The processor board may be configured to detect the type of lead assembly, to measure skin resistance, to generate the appropriate voltage/current pulses and the operational amplifiers and analog to digital converters required for the sensors. The monitor can display graphs of TOF signals sensed using the methods or systems described herein, including noise correction methods.

The lead assembly 105 may include an accelerometer, a flex circuit, a plurality of spaced apart electrodes and a connector to connect to the monitor. The lead assembly 105 may be configured to be an accelomyography based sensing device, an electromyography based sensing device, or both. The monitor 101 can sense the type of lead assembly 105 when the lead assembly is connected to the monitor through the connector.

The monitor 101 through the lead assembly 105 may provide quantitative twitch monitoring using a plurality of discrete stimulation pulses and sensing the patient's response to each of these stimulation pulses. This is performed over a set time period, e.g., less than 5 seconds, less than three seconds, about two seconds, or the like. In an example, the stimulation pulses can be four electrical impulses within a two second time span (a "train-of-four" or TOF). The lead assembly 105 applies these stimulation signals to a nerve that may cause the patient to move slightly, or twitch. The lead assembly 105 can apply the stimulation pulses to the ulnar nerve near the wrist. The lead assembly 105 then senses the patient's response to the stimulation signals at the thumb and forefinger, e.g., the thumb and forefinger to twitch. The TOF count describes the number of identifiable responses following the TOF stimulation pattern. Without neuromuscular blockade, all four responses are of essentially equal amplitude. Loss of the fourth response represents a 75-80% neuromuscular blockade. Disappearance of the third, second, and first responses is associated with 85%, 90%, and 98-100% neuromuscular blockade, respectively. A train-of-four ratio is obtained by dividing the amplitude of the fourth response by the amplitude of the first response as a measure of neuromuscular recovery. A ratio of 0.7 represents adequate diaphragmatic recovery (i.e., the ability of the patient to breathe). A ratio of >0.9 ensures sufficient pharyngeal muscle recovery for extubation. Improvements in monitoring the neuromuscular blockade may result in improved patient treatment and outcomes.

The monitor 101, or optionally the base 102, communicates through a network 107 to a server 110. The server 110 can store data from the monitor 101 and electronic medical records. The data can include sensed data, TOF data, electrical noise data, neuromuscular block data electromyography data, stimulation signal data, post tetanic count data, single twitch data, accelerometry data and the like. In an example, the base 102 may provide a wireless (inductive) charging to the monitor 101. This will reduce the need to change batteries, while also protecting the patient from current surges they could experience from a monitor 101 plugged directly into the mains in the wall. The base 102 may also connect to the hospital's electronic medical record (EMR), communicate wirelessly with the monitor 101 to receive twitch monitoring data, and transmit this data wirelessly or via a cable to the EMR through the network 107.

The monitor 101 and lead assembly 105 are portable and stand alone when in use. The lead assembly 105 can be applied to a patient before an anesthetic drug is administered to the patient. The lead assembly 105 can remain on the patient through recovery, e.g., in the post anesthesia care unit (PACU). The monitor 101 may also travel with the patient. In an example embodiment, a first monitor can remain with the surgical suite and removed (e.g., unplugged) from the lead assembly 105 when the patient leaves the surgical suite. A second monitor can be plugged into the lead assembly 105 outside the surgical suite (e.g., at the PACU).

The monitor 101 can use impedance measurements to identify potential problems with the electrical connections to the electrodes and the electrodes themselves. The monitor can also detect a poor electrical connection to the patient's body. The monitor 101 can also use a measurement of the impedance to distinguish between two low signal conditions. A first low signal condition may be caused by problems with the electrodes or electrode connections. A second low signal condition may occur when total paralysis of the patient is reached. The impedance includes the impedance of the device and the human body. The impedance of the device includes the internal impedances of the monitor and the impedances of the leads, e.g., connections, wires and electrodes. The impendence of the device can be determined during manufacture and stored in the memory of the monitor. The impedance of the human body, e.g., the patient, is generally defined as $R_{total} = R_{Skin}(in) + R_{internal} + R_{skin}(out)$. $R_{total}$ can be used when calibrating the monitor to a specific patient by applying a signal through the body between two electrodes. The human body impedance includes the resistance of dry skin, which may be between about 1,000-100,000 Ohms. The skin's resistance is much lower if it is wet or burnt/blistered. In some examples, it is desirable to apply a conductive paste or conductive gel to assist in applying the electrode to a patient with good electrical conductance. A medical grade electrically conductive gel may include an aqueous solution with concentrations of ionized salts as the conducting agent, a natural gum capable of crosslinking, and a crosslinking material which provides the electrically conductive gel with sufficient internal strength to remain cohesive without reinforcement. Impedance can be measured, for example, by applying a known signal at a first electrode and sensing the response at another electrode. The monitor can test each electrode using an signal source and sense the resulting signal at any one or multiple other electrodes. This may be used to calculate the impedance of the signal paths to the patient and through the patient to the desired nerve to be stimulated.

If the lead impedance is above a threshold, which can be stored in the monitor, then the monitor may determine that there is a problem with the electrodes or electrode connections. The monitor may issue a signal, e.g., a light or other display indicia, that there is an issue with the electrical connection and may not be able to acquire an assured signal. If the impedance is normal, the low signal is likely a result of patient paralysis. In both low signal cases, the accelerometer signal or EMG signal is very low. In both cases, the monitor will not calculate a TOF ratio (in an example, the monitor will instead display the TOF count as zero), as the low signals may result in an erroneous TOF ratio. For example, if the sensed signal is very low, for example, less than 10% of the original sensed signal amplitude or less than a fixed value, (e.g. an EMG amplitude less than 2 mV) and about equal in all four twitches, as would be the case for deep paralysis, the TOF ratio may be incorrectly displayed as 100% (meaning the fourth twitch is the same amplitude as the first twitch), which implies that the patient is unparalyzed, when in fact the patient is completely paralyzed.

The monitor 101 further may include a modality selection functionality that selects the electrodes for use in neuromuscular block detection. With the use of multiple electrodes, the monitor 101 selects the stimulation electrode and/or the sensing electrode from the multiple electrodes. The monitor can use any of the electrodes positioned at a stimulation target nerve to apply a stimulation signal. The monitor can use any of the electrodes positioned at a stimulatable muscle to sense a stimulation of the muscle, either electrically or by mechanical movement. The monitor can also select one of the non-selected electrodes to remove common mode signals from the sensed signal. A common mode signal may include environmental noise, e.g., a 60 Hz signal from a power main or other device in the surgical theatre that is present in the patient's body. The monitor may include circuitry to sense the common mode signal, apply a gain to the common mode signal and subtract the common mode signal from a sensed signal, e.g., by inverting the common mode signal and adding it to the sensed signal. In an example with three sensing electrodes, the with a first electrode on the palm, the second electrode being on the back of the hand, and the third being on a finger, the monitor 101 will select the best electrode for sensing. One of the other electrodes will be a common mode electrode, which will be used to suppress the common mode signal. The signal being sensed is the difference between the electrodes. Accordingly, the common mode signal should be suppressed.

In an example, a stimulation electrode is stimulated and the first electrode is the detection electrode. The first value of this detection is sensed and saved. The stimulation electrode is stimulated and the second electrode is the detection electrode. The second value of the second detection is sensed and saved. The first value is compared to the second value. The larger of the first value or the second value determines the use of the electrodes, either the first electrode or the second electrode is selected, respectively. The other of the first electrode and the second electrode is the common mode electrode. The third electrode in each of these cases is negative electrode for EMG detection. These electrodes can also be used to detect a noise signal that may be part of the sensed TOF signal.

The monitor 101, in its modality selection, may further decide between electromyography detection and/or accelerometer detection. The monitor 101 may receive an input through a machine human interface that selects the type of detection between the electromyography detection or the accelerometer detection.

The base 102 can be integrated into an anesthesia machine. The monitor 101 can be an accessory of the anesthesia machine. The base 102 may include a wheeled cart that includes a plurality of drawers. At least one of the drawers may be locked to store certain drugs. The base may further include network communication connections, e.g., to electronic medical records database(s). The base may also include other electrical connections, e.g., USB and the like. The base 102 may also include a horizontal workspace. In an example, the monitor 101 may be electrically connected to the base through the electrical connections at a monitor support that is separate from the workspace.

The monitor 101 can include a calibration routine that gradually raises the stimulation current applied to the patient through the lead assembly 105 until further increases in current do not result in a larger muscle twitch. The stimulation current is then set to just over this maximal stimulation current, e.g., supramaximal stimulation. In operation, the calibration should be performed on the patient before administering paralyzing drugs. The monitor will apply continually increasing pulses in a series of single pulses spaced about or at least one second apart. However, such a calibration sequence does not work in paralyzed patients, as the neuromuscular blockade results in a fade (decrease) in the response to single twitches spaced this close together, which confounds the ability to detect the maximal signal amplitude. In the case where a patient is already paralyzed by the drug, the monitor 101 will use a sequence of pulses where the single pulses are spaced further apart. In an example, the first twitch in a TOF sequence is spaced at least ten seconds from the end of the preceding TOF sequence. The monitor will monitor the TOF ratio to make sure the patient's paralysis level does not change over the course of the calibration sequence, which would also confound the data and prevent calibration. An example sequence includes (1) start the first TOF calibration at 25 m A; (2) measure the T1 height of two successive TOF sequences spaced at fifteen second intervals; (3) assuming the TOF ratio is constant and also checking to see if the patient is sufficiently "unparalyzed", e.g. TOF>0.4 which correlates to T1 50% of baseline, increase the amplitude in steps of 5 mA until the T1 twitch height does not increase further (<5% increase); and (4) take the amplitude that preceded the plateau (e.g., 40 mA) and multiply this by 110% (e.g., 44 mA) and use this as the "supramaximal current" for all subsequent stimulation.

In use, the monitor 101 and the lead assembly 105 can operate to stimulate and sense the patient response. One example of the more sophisticated type of stimulation afforded by quantitative twitch monitoring by the monitor 101 and the lead assembly 105 is the train-of-four (TOF) stimulation sequence and calculation of a train-of-four ratio. A train-of-four sequence involves applying four distinct electrical impulses within a time span, e.g., two seconds. The impulse train is the stimulation signal and is generated by circuitry in the monitor. The lead assembly delivers the stimulation signal to the patient, e.g., to the ulnar nerve near the wrist, which causes the thumb, the forefinger, or both to "twitch", once for each of the four electrical impulses (in the unparalyzed patient). The TOF count describes the number of identifiable responses following the TOF stimulation pattern. Without neuromuscular blockade, all four responses are of equal amplitude. With increasing neuromuscular blockade, the fourth, third, and then second responses start to become smaller in amplitude (called "fade"). A train-of-four ratio is obtained by dividing the amplitude of the fourth response by the amplitude of the first response as a measure of neuromuscular blockade. A ratio of 0.7 (70%) represents adequate diaphragmatic recovery (i.e., the ability to breathe). A ratio of >0.9 (90%) ensures sufficient pharyngeal muscle recovery for extubation. The present system and method provides quantitative twitch monitoring to provide precise characterization of the level of paralysis.

The lead assembly 105 quickly allows a medical professional to place the sensing electrodes at least one (or more) muscle-recording sites. The lead assembly supports its electrodes in a prepositioned manner. The monitor 101 uses an algorithm to select the best sensing site based on signal analysis. The monitor can select the best electrode to use from the plurality of electrodes that are pre-packaged in the lead assembly.

The monitor 101 can sense and process signals from both electromyography ("EMG") electrodes and an accelerometer. The algorithm in the monitor 101 can pick the sensing mechanism that gives the best signal. The monitor 101 may auto-detect the best sensing location from a plurality of sensing locations (e.g., an electrode placed over the first dorsal interosseous muscle vs. the adductor pollicis muscle) based on, for instance, maximal signal height, maximal area-under-the-curve, waveform analysis or other signal processing analysis. The monitor 101 may also notify the user if a lead is bad and which electrode or lead is faulty, e.g., based on impedance measurements.

The monitor 101 can also plot a time course of the sensed data from the lead assembly 105. The monitor can calculate a prediction of a patient's time to complete recovery or a time to a train-of-four ratio to exceed a set value, e.g., "time to TOF>0.7" or "time to TOF>0.9." This prediction may be an estimate based on an extrapolation of the prior twitch monitoring data for that specific patient, as every patient has different recovery times from neuromuscular blockade. Alternatively, the prediction may be based on a prior history of similar patients with similar profiles e.g., height, weight, age, sex, diagnosis, etc.

The monitor 101 can also use more sensitive algorithms for sensing the patient's state when the patient is significantly paralyzed (e.g., TOF=0, or <0.1), a more sensitive sequence, e.g., post tetanic count (PTC) can be used to quantify deep paralysis. The monitor 101 will detect TOF=0, and switch automatically to PTC monitoring. The monitor 101 can output a plot of both on a time plot on a display. If significant neuromuscular recovery occurs, the monitor 101 will switch back to TOF from PTC.

Figure 2A:
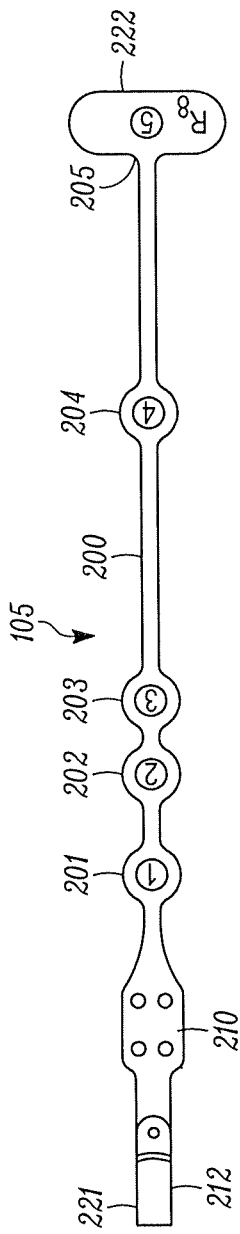
FIG. 2A shows a view of a lead system for use in neuromuscular monitoring according to an example embodiment.

FIG. 2A shows a lead assembly 105 that includes a base 200 and a plurality of electrodes 201-205 supported on the base 200. The base 200 is elongate with a proximal end 221 that is adjacent the monitor and a distal end 222. The proximal end 221 can include a connector 212 to electrically connect the lead assembly 105 to the monitor 101. The base 200 can include a flexible substrate supporting a plurality of conductors, e.g., metal trace lines, printed conductive inks, wires, and the like, which extend from the connector 212 to the respective electrode 201-205. The underside of the base 200 may include medical grade adhesive to fix at least parts of the base to the patient. The base 200 may include a peripheral body around each of the electrodes 201-205. As a result, the base 200 is wider at the electrodes 201-205 than between the electrodes. The electrodes 201-205 electrically contact the patient and are held in place by the base 200.

The first electrode 201 is the closest electrode to the proximal end 221. The first electrode 201, the second electrode 201, and the third electrode 203, are sequentially positioned from the proximal end 221 and can each apply a stimulation signal to the ulnar nerve. The monitor 101 can determine which of the one or more than one electrodes 201-203 is best to apply the stimulation signal to the patient's ulnar nerve. Each of the electrodes 201-203 or select ones of the electrodes 201-203 receive a stimulation signal from the monitor or other control unit. The stimulation signal can be up to about 400 volts to create a 50 milliamp signal in the patient at the ulnar nerve or other nerve to be stimulated. One of the electrodes 201-203 may be connected to earth and not be directly driven by the stimulation signal.

The electrode 204 is configured and positioned to detect response of the patient to the stimulation signal applied by the other electrodes 201-203. The signal detected by the electrode 204 is fed back to the monitor over conductors for analysis and quantitatively determining a level of neuromuscular blockade. The electrode 204 may be positioned at the adductor pollicis muscle or the first dorsal interossei muscle to detect muscle activity thereof in response to the stimulation signal.

Figure 2B:
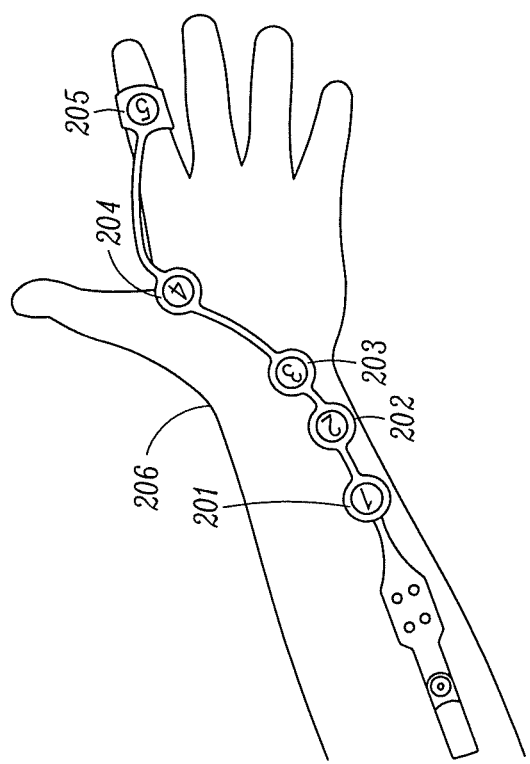
FIG. 2B shows a view of a lead system as applied to a patient for use in neuromuscular monitoring according to an example embodiment.

The electrode 205 is positioned near the end of a finger, e.g., the index finger as shown in FIG. 2B. The electrode 205 can be about 14 centimeters from the proximal end 221. The electrode 205 can be a neutral (negative) terminal.

An accelerometer can be placed with or in place of any one of the plurality of electrodes 201-205. In an example, the accelerometer is positioned at the fourth electrode 204 at the adductor pollicis muscle or the first dorsal interossei muscle and can sense movement of the associated muscle in response to the stimulation signal applied by at least one of the first electrode 201, the second electrode 202 or the third electrode 203. In an example, the accelerometer is placed at an electrode on a finger of the patient. In an example, the accelerometer is a separate device to be positioned at the end of a finger. The accelerometer can be integrated in the lead assembly base 200.

Application indicia 210 can be proved adjacent the proximal end 221 of the lead assembly base 200. In the case where the lead assembly base 200 is adapted to be applied to either hand of the patient, the indicia 210 can show the proper application for both the left hand application of the lead assembly and the right hand application of the lead assembly. The indicia are graphical representations of the location of the each of the plurality of electrodes 201-205 when applied to either hand. The lead assembly base 200 can have an adhesive on one side to removably adhere the base 200 to the patient. An electrically conductive adhesive can be positioned at the electrodes.

The electrodes 203, 204, and 205 may be positioned at other locations on the patient's hand. In an example, at least one electrode may be positioned on the little (sometimes referred to as the pinky) finger of the patient. As described herein the stimulation electrodes 201, 202 stimulates the ulnar nerve, which is a large not protected by muscle or bone in the human body. The ulnar nerve is the only unprotected nerve that does not serve a purely sensory function. The ulnar nerve is directly connected to the little finger, and the adjacent half of the ring finger. Thus, placing the sensing electrodes adjacent the little finger or on the little finger may provide improved stimulation and sensing for some patients.

Figure 3:
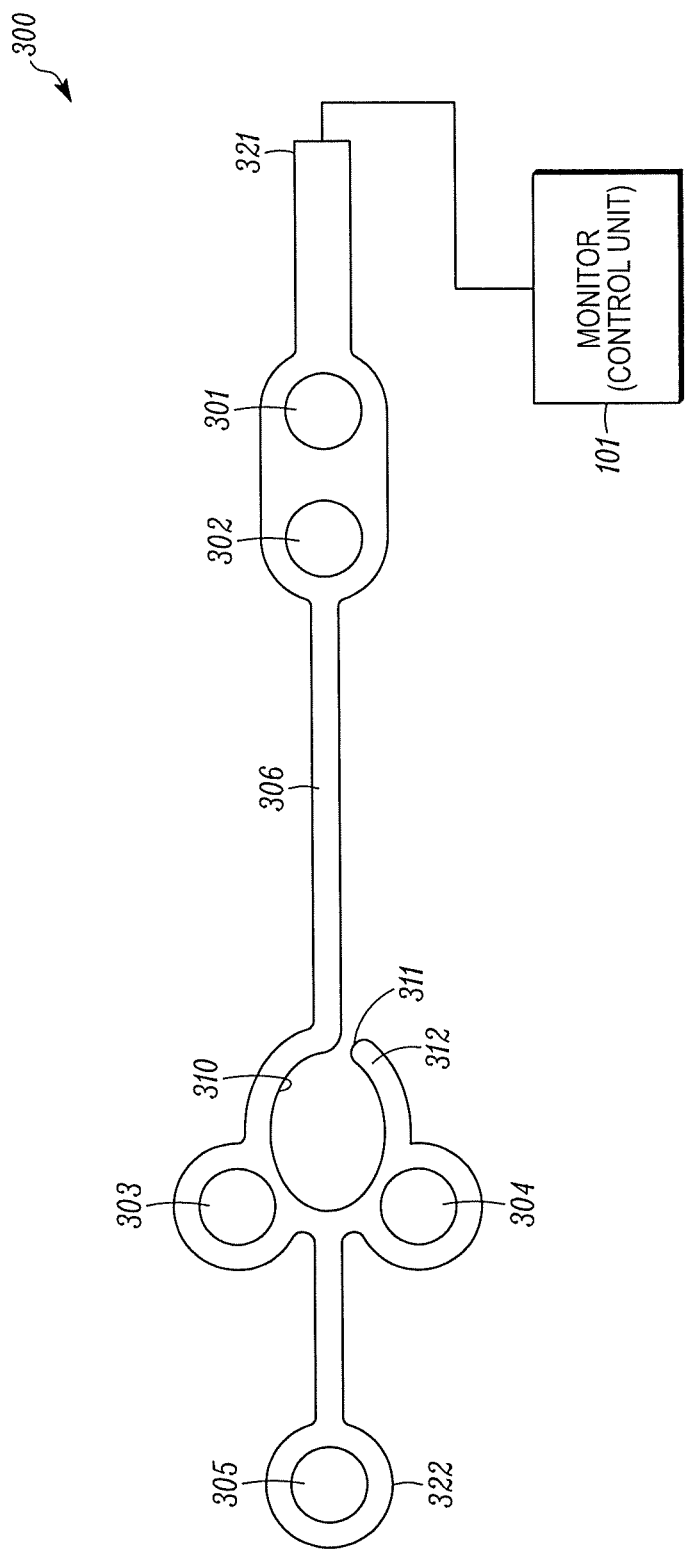
FIG. 3 shows a view of a lead system for use in neuromuscular monitoring according to an example embodiment.

FIG. 3 shows a lead assembly 300, which is another embodiment of the lead assembly 105. The lead assembly 300 includes a plurality of electrodes 301-305 supported on a base 306. The base 306 can be formed of material similar or the same as those in the base 200 of the FIG. 2A embodiment. The base 306 can include an adhesive on one side thereof to removably fix the lead assembly 300 to a patient. An electrically conductive adhesive can be positioned at the electrodes 301-305.

The base 306 is elongate and extends from a proximal end 321 to a distal end 322. The base 306 is non-rigid and flexible to curve along the anatomy of a patient, e.g., a wrist and hand. A plurality of conductors extends within the base 306 and electrical connect the monitor to the electrodes 301-305. The first two electrodes 301, 302 are stimulation electrodes that apply a stimulation signal, e.g., a train of electrical pulses, to a nerve of the patient (e.g., the ulnar nerve, posterior tibial nerve or the facial nerve). Two sensing electrodes 303, 304 are positioned intermediate the proximal and distal ends 321, 322. In an example, the sensing electrodes 303, 304 are closer to the distal end 322 than the proximal end 321.

The electrodes 301-305 operate to provide a surface electromyography reading to assess the patient's muscle function by recording muscle activity from the surface above the muscle on the skin. The electrodes 303, 304 can read activity of the adductor pollicis muscle, the dorsal interossei (e.g., the first dorsal interosseus), the orbicularis oris muscle, or the flexor hallucis longus muscle, etc. The electrodes 303, 304 are surface electrodes and are able to provide only a limited assessment of the muscle activity in response to a stimulation signal from the stimulation electrodes 301, 302. A further negative electrode, e.g., electrode 305 at the patient's finger, is used to determine the EMG signal. While shown as two electrodes for sensing, in an example, more than two electrodes can be used to record the muscle response to the stimulation signal. In an example, the response can be recorded by a pair of electrodes or by a more complex array of multiple electrodes. However, more than one electrode is needed as EMG recordings display the potential difference (e.g., voltage difference) between two separate electrodes. In an example, the other of the electrodes 303 or 304 that is not adjacent the muscle being stimulated can be a driven electrode to suppress common mode signals. The electrode 305 can be used as the negative electrode to provide the voltage difference for the EMG signal. It is desirable to select which of the electrodes 303, 304 is going to be used to detect a patient response. The electrode that shows the best conductivity or the best response to a test signal can be selected by the monitor 101 as the sensing electrode. Simply stated, there may be two modes, the first mode includes the electrode 303 suppressing the common mode signal, the electrode 304 being the positive EMG detection electrode, and the electrode 305 being the negative EMG detection electrode. The second mode includes the electrode 303 being the positive EMG detection electrode, the electrode 304 detecting the common mode signal, and the electrode 305 being negative EMG detection electrode.

An electrical connector is provided at the proximal end 321 to connect the electrodes to a monitor or control unit 101 through an electrically conductive wire. The monitor/control unit 101 includes control circuitry to processes and output electrical signals related to stimulation and sensing of electrical signals at the patient. The monitor/control unit 101 can include a rechargeable battery that can power the system when not plugged into a mains power source. The monitor/control unit 101 can include a display screen with tactile input circuitry integrated therein. The display screen is configured to output any of the graphical user interfaces described herein. The display screen can toggle between showing a sensed EMG signal or a time plot of ongoing train of four testing. When producing valid results, the TOF calculated values can be shown in the display screen.

In operation, the monitor may include circuitry to detect the common mode signal. The circuitry inverts the common mode signal and then applies a gain to produce a common mode suppression signal. The common mode suppression signal is applied to the non-sensing electrode to suppress the common mode signal.

The electrodes 303, 304 are positioned distally over a thumb aperture 310 in the base 306. The thumb aperture 310 is formed by an oval shaped extension of the base 306, which wraps around the thumb aperture 310 and extends back toward the proximal end. An insertion opening 311 is defined between the main body of the base 306 and a cantilevered arc 312 of the base 306. It will be within the scope of the present disclosure to provide the thumb opening of different shapes, e.g., circular, or polygonal. In an example, the thumb opening 310 is closed, i.e., it does not have a gap 311 and an end of the arc 312 extends back to the intermediate part of the base 306.

The electrode 305 is at the distal end 322. The electrode 305 may be a neutral electrode and positioned on an end of a finger, e.g., the index finger of the patient.

The lead assembly 300 is affixed to a patent with the electrodes 301, 302 on the skin over the ulnar nerve. The thumb of the patient extends through the thumb aperture 310. The electrodes 303, 304 are positioned on the opposite sides of the hand. When the lead assembly 300 is positioned in the patient's left hand, then the electrode 303 is on the palmar side and electrode 304 is on the dorsal side. The opposite is true when the lead assembly 300 is mounted on the patient's right hand, e.g., the electrode 303 is on the dorsal side and the electrode 304 is on the palmar side. The sensing electrodes 303, 304, depending on the side they are positioned sense the movement of the adjacent musculature. The other of the electrodes operates as a driven electrode, which can sink or source current. The use of the driven electrode can reduce common-mode interference. The circuitry in the monitor may detect the common mode signal in the patient. The common mode signal may be used in the monitor to remove the common mode signal from the sensed signal due to muscle activity or may be applied to the non-sensing electrode to suppress the common mode signal.

When the lead assembly is placed on a patient, the medical professional can input into the monitor 101 the hand on which the lead assembly is affixed, e.g., through a machine to human interface or other I/O device. This will assist the monitor 101 in reading the response from the associated muscle.

The base may 300 may be formed of different shapes to move the electrodes to different positions on the patient's hand. For example, when an electrode, e.g., electrode 305, is to be positioned on a finger other than the index finger, e.g., the little finger, the base will be shaped such that the portion extending from the thumb extends across the back of the patient's hand or palm to extend to the little finger.

The electrodes 201-205 and 301-305 may be self-preparing electrodes that have an electrolytic substance, e.g., a gel, on the electrodes to improve electrical contact to the patient. The electrodes may also include small tines or microneedles that are of a length to extend into the stratum corneum. The stratum corneum may interfere with some electrical signals and penetrating or scraping off some of the stratum corneum may improve electrical stimulation or sensing functions of the electrodes. The microneedle or tines of the electrode may pierce the stratum corneum up to or through dermis of the skin. As a result, an electrical signal passes or is conducted through or across the electrode past stratum corneum with a reduced impedance relative to being on the surface of the stratum corneum.

Figure 4:
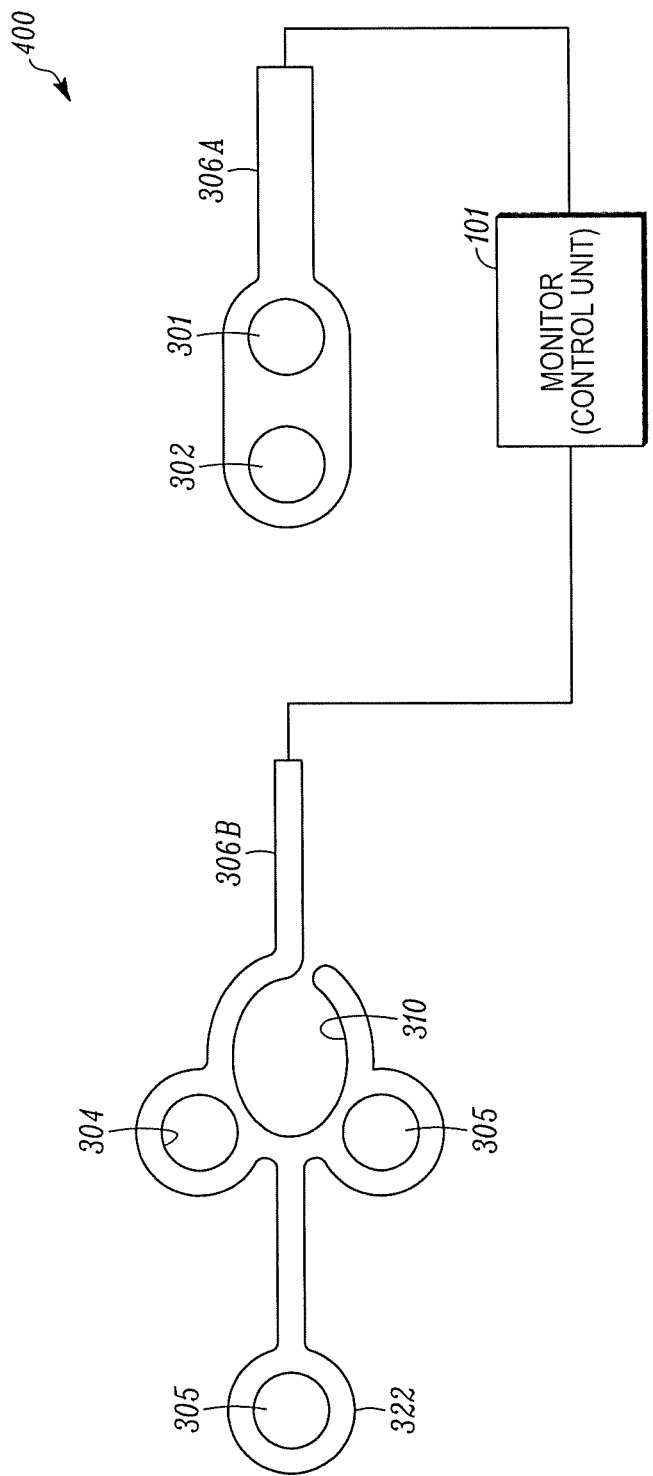
FIG. 4 shows a view of a lead system for use in neuromuscular monitoring according to an example embodiment.
Figure 9:
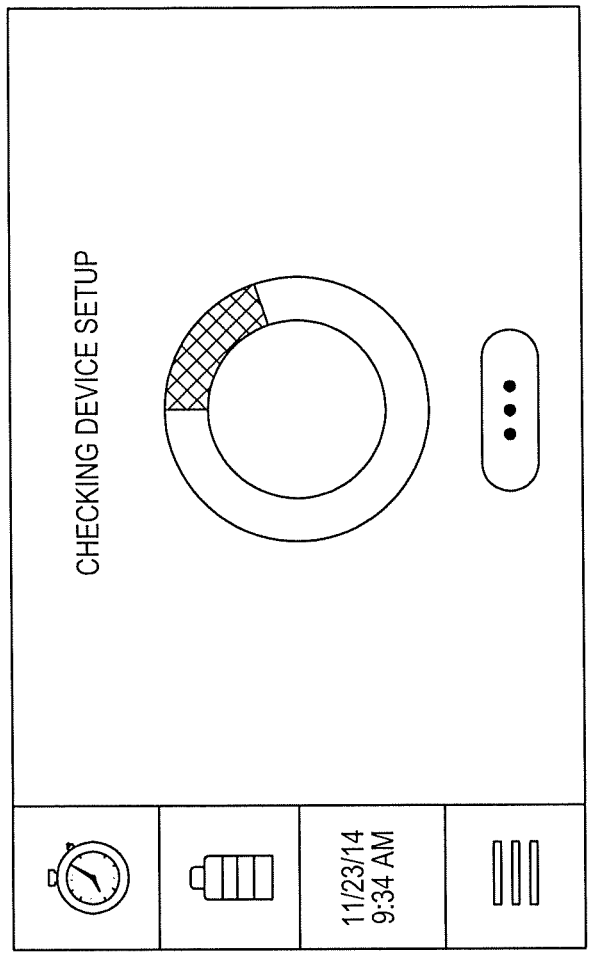
FIG. 9 shows a schematic view of a control unit for a neuromuscular monitoring system according to an example embodiment.

FIG. 4 shows a lead assembly 400 that is similar to the lead assembly 300 but with a different base 306A, 306B. The same elements are shown with the same reference numbers as used in FIG. 3 and similarly being designated with a same reference number and a suffix "A" or "B." The base 306 (FIG. 3) is separated into two separate bases 306A, 306B. The proximal, stimulation base 306A supports the stimulation electrodes 301, 302 and electrically connected the electrodes 301, 302 to the monitor 101. The distal, sensing base 306B supports the positive sensing electrodes 303, 304 and the negative electrode 305. The sensing base 306B also forms the thumb aperture 310. The sensing base 306B electrically connects the electrodes 301, 302 to the monitor 101. The physical separation of the sensing electrodes 303, 304 from the stimulation electrodes 301, 302 may allow for easier application to the patient. The separation of the electrical paths for the stimulation and the sensing between the lead assembly 400 and the monitor 101 may reduce cross talk between the conductors and may result in a better sensed signal from at least one of the sensing electrodes 303, 304.

FIG. 5 shows a graphical user interface 500 that is shown on a display that is part of the monitor 101. The interface 500 shows the monitor checking its set up and connection with the lead assembly 105. A progress graphic 501 can show the progress of the check device process. The battery charge and the time can be shown in a header 503. The TOF ratio and timer can be shown in a first display area 505. The current view name can be shown in a second display area 507. The progress graphic 501 and the control button 508 are in a third display area 509. The control button 508 is inactive, e.g., shown as greyed out or with other indicia to indicate that the device is not active yet.

FIG. 6 shows a graphical user interface 600 that is shown on a display that is part of the monitor 101. Interface 600 is at a settings stage, which is at a further stage of operation relative to interface 500. The current settings 601 are shown in the third display area 509 with the control button 508 being active as start button. Each of the settings 601 can be selected and changed through interaction with the display, if it is a touchscreen, or by using an input/output device connected to the monitor 101. The stimulation signal parameters can be adjusted. The stimulation parameters may include the current, the pulse width, the frequency and the monitoring mode. The current as shown in interface 600 is set at 50 mA. The pulse width as shown in interface 600 is set at 200 microseconds. The frequency as shown in interface 600 is set at 10 seconds. The mode as shown in interface 600 is set at train of four (TOF).

FIG. 7 shows a graphical user interface 700 that is shown on a display that is part of the monitor 101. Interface 700 is at a stimulation stage, which is at a further stage of operation relative to interfaces 500 and 600. The first display area 505 shows the reading of TOF ratio, here as 90%. The third display area 509 shows the train of four results as a bar graph 701, with each bar being a reading at times T1, T2, T3, and T4. A settings icon 703 is provided to allow the user to return the process back to the settings stage as shown in FIG. 6. The control button 508 is now a pause button to stop the stimulation and reading of the results by the monitor 101.

Figure 8:
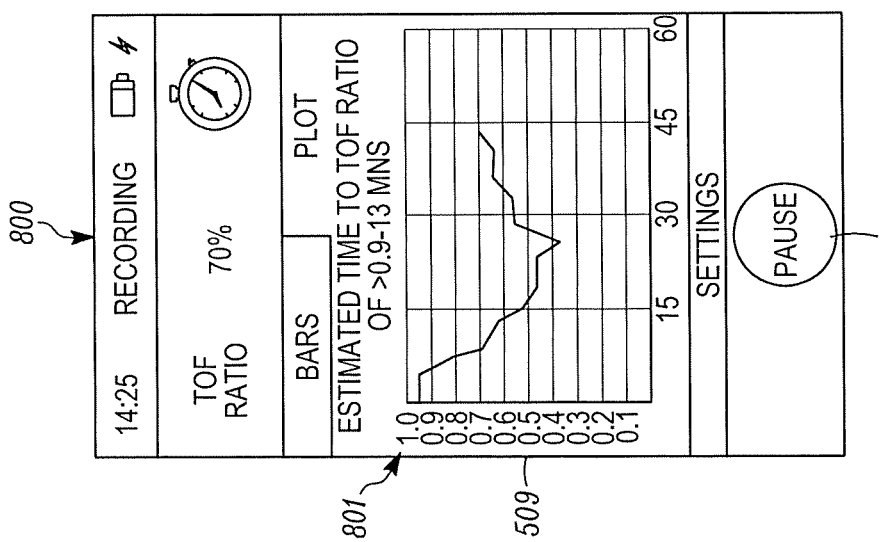
FIG. 8 shows a schematic view of a control unit for a neuromuscular monitoring system according to an example embodiment.
Figure 10:
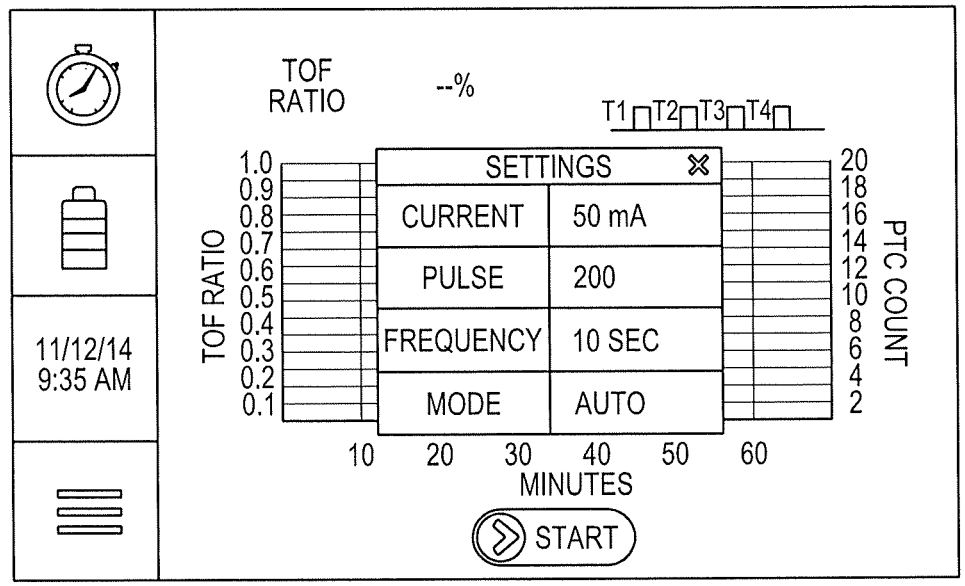
FIG. 10 shows a schematic view of a control unit for a neuromuscular monitoring system according to an example embodiment.
Figure 11:
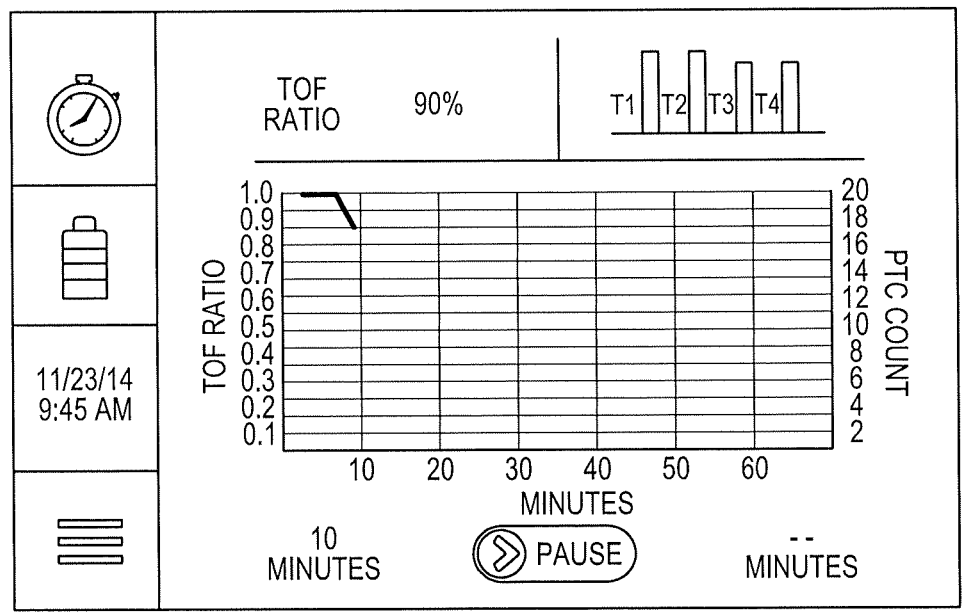
FIG. 11 shows a schematic view of a control unit for a neuromuscular monitoring system according to an example embodiment.
Figure 12:
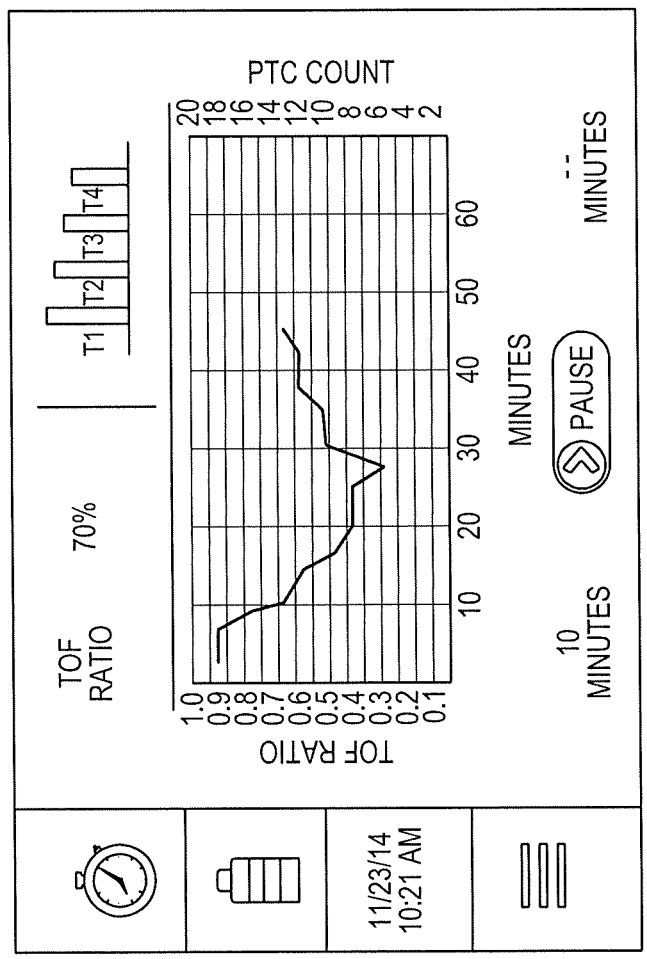
FIG. 12 shows a schematic view of a control unit for a neuromuscular monitoring system according to an example embodiment.

FIG. 8 shows a graphical user interface 800 that is shown on a display that is part of the monitor 101. Interface 800 is at a recording stage, which is at a further stage of operation relative to interfaces 500, 600 and 700. Interface 800 shows the plot of the data 801 in the third display area 509 in place of the bar chart as shown in FIG. 7. The readings in the FIG. 8 example have a TOF ratio of 70%. The plot can be the TOF ratio over the time. At time $T_0$ (left most point in the abscissa), the patient is not yet subject to anesthesia or not yet experiencing neuromuscular blockade. The TOF ratio is at 1.0 or 100%. At the time where the TOF ratio begins to drop is when the patient is subjected to neuromuscular blockade. In this example, the lowest TOF ratio is at about 25 minutes with a TOF ratio of about 0.4 or 40%. The monitor can further calculate a predicted time until the TOF ratio is at 0.9. Here this is shown as 13 minutes. The monitor can employ a processor that applies various rules to the data to determine the predicted time to the TOF ratio achieving 0.9. The processor may apply a curve fit rule or the like to predict the TOF ratio over time. However, the medical professional still determines when the patient is at the appropriate state to be woken and may use the prediction as a factor in deciding to wake the patient along with other factors, e.g., redosing of the neuromuscular blocking drugs, drug changes, blood transfusion, etc.

FIGS. 9-12 show the same steps in the monitoring process as in FIGS. 5-8 but at a further display, which may be on or in communication with additional medical device, e.g., the base 102 or the server 110. This will allow additional medical professional to monitor the patient condition remote from the monitor 101 and possibly the patient.

Figure 13:
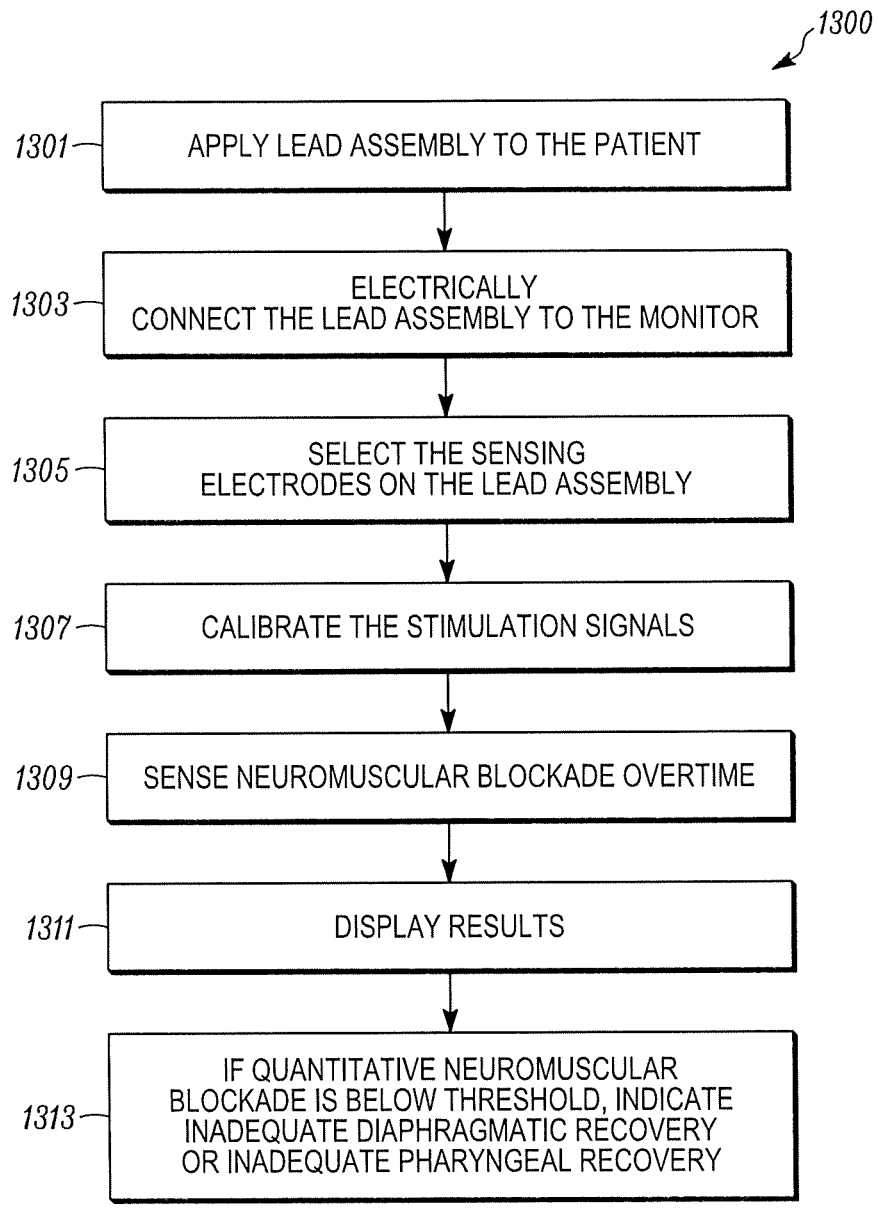
FIG. 13 shows a flow chart showing a neuromuscular monitoring process according to an example embodiment.

FIG. 13 shows a process 1300 for monitoring a patient under anesthesia with neuromuscular block. At 1301, the lead assembly is applied to the patient. At least two excitation electrodes are positioned over the nerve to be stimulated. Two or more electrodes are positioned over muscles that may be stimulated by the stimulation signals. At 1303, the lead assembly is electrically connected to the monitor, which will generate the stimulation signal and process the response signals sensed by the lead assembly.

At 1305 the monitor selects the electrodes on the lead that will be used to sense the neuromuscular blockade in the patient. The monitor may measure impedance values of each of the electrodes. For example, with reference to FIGS. 3 and 4, the impedance between the electrode 303 and the electrode 305 is measured. The impedance between the electrode 304 and the electrode 305 is measured. The impendence value that falls within an acceptable range is selected. The impedances relative the sensing electrodes 303, 304 can be otherwise measured by the monitor.

At 1307, the stimulation signals are calibrated. In an example, the calibration can be performed before the patient is administered paralyzing drugs. In another example, the patient has already received a paralyzing drug. The monitor can step through successive input signals until the measured patient response stops increasing. The input signal starts at a low value and will sequentially increase by a set amount. The successive input signals can start at about twenty five mA and increment by five mA until an increase in current no longer causes an increase in the detected response. If a TOF input signal is used, then the first impulse response (T1) is used to determine a change in the patient response. The TOF ratio is used to verify that the patient's paralysis level remains constant during the calibration. If the TOF ratio is constant at successive input signals, the input value is increased until an increase in input signal no longer results in an increase in the detected response. The calibration sets the maximum input signal value (the stimulating current). In an example, the maximum input signal is the input signal value where the patient response plateaued increased by a factor. The factor can be added to the signal or multiplied by the signal. Increasing the maximum input signal helps to ensure that the maximum value is not below the patient's threshold and a response will occur when the paralyzing drug's effect on the patient is reduced. An example of a TOF determination is further described with reference to FIG. 18.

The step 1307 can also operate to determine a noise floor value. The ambient noise sensed by the sensors on the patient is sensed. Over a time period, the electrical signal at the sensors on patient is sensed. No stimulation signal is applied to the patient during this noise floor sensing time period. The noise floor value can represent stray electrical signals that are sensed at the patient. The noise floor value can be the lowest value that represents an electrical response from the patient due to a stimulation signal. Sensed values at or less than the noise floor value may be discarded when performing calculations and patient status output relating to sedation of the patient.

At 1309 the neuromuscular blockade is sensed over time. The continuous sensing allows the medical profession al to see the trends, past state and current state of the patient and the effects of the drugs.

At 1311, the monitor can display the sensed data, the settings or the calculated results. The display can include the calculated value, e.g., a TOF ratio or percentage, or the plot of the data over time.

At 1313, the monitor can determine if the patient state as measured as a quantitative value is below a threshold, the monitor can indicate that the patient is not yet recovered from the drug. For example, the threshold can indicate that the patient has inadequate diaphragmatic recovery or inadequate pharyngeal recovery.

Figure 14:
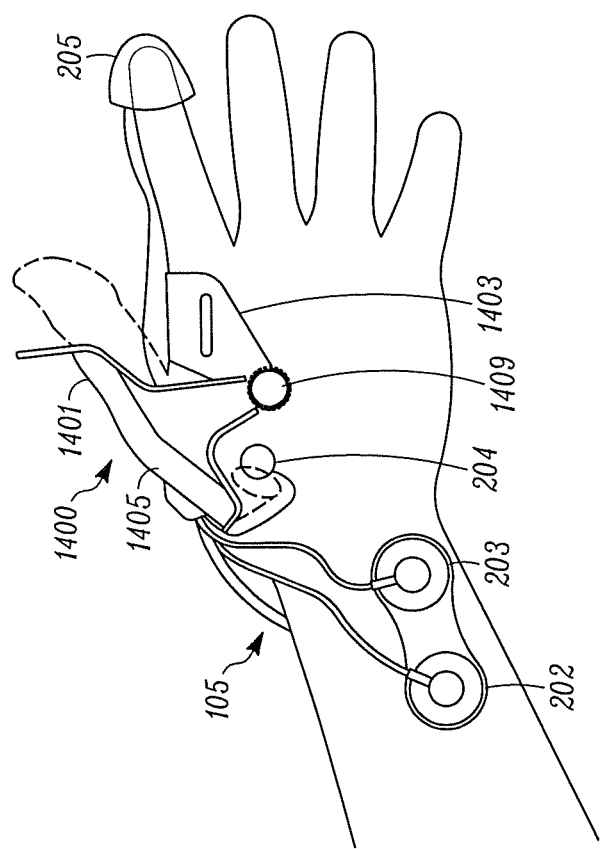
FIG. 14 shows a view of neuromuscular monitoring system according to an example embodiment.

FIG. 14 shows a quantitative twitch monitoring system 1400 with a lead assembly 105 combined with a twitch sensor 1401. The lead assembly 105 may include similar electrodes as those described above with reference to FIGS. 2A and 2B. The twitch sensor 1401 includes a hand support 1403 mounted over the side of the patient's hand adjacent the thumb and index finger. The support 1403 includes a first wall on the palmar side of the hand and a second wall on the dorsal side of the hand to secure the support to the patient. The support 1403 is fixed in place, e.g., using an adhesive. A twitch sensor body 1405 is pivotally connected to the support 1403 through an adjustable tensioning pivot 1409. The patient's thumb is held within the twitch sensor body 1405. An accelerometer is integrated into the twitch sensor body 1405. When the patient's thumb moves in response to stimulation, e.g., by the electrodes 202, 203 on the ulnar nerve, the twitch sensor body 1405 will move and the accelerometer will sense the movement and output a signal on the cable to the monitor 101. It will be within the scope of the present disclosure to use the twitch sensor 1401 with only stimulation electrodes 202, 203 and not sensing electrodes 204, 205.

Figure 15:
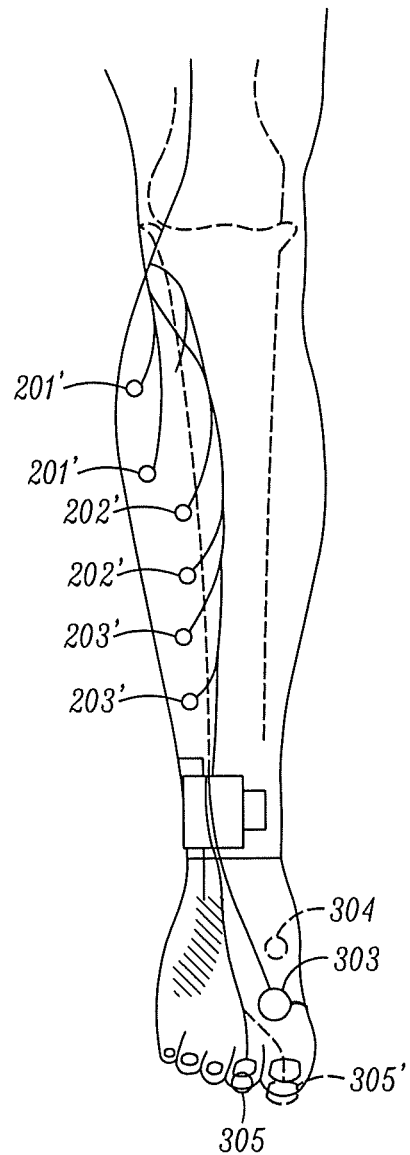
FIG. 15 shows a view of neuromuscular monitoring system on a leg according to an example embodiment.

It is within the scope of the present disclosure to use the monitoring system on different parts of the body, e.g., the leg or the face. FIG. 15 shows a monitoring system 1500 with the lead assembly 105 on the foreleg and the foot of the patient. The stimulation neuromuscular electrode is placed on the lateral anterior surface of the lower leg 1501 proximal to the ankle joint 1503. The physical dimensions of the electrode are chosen from a predetermined set of dimensions which are optimized for the range of ankle joint sizes found in adults. There can be two stimulation electrodes at different sites overlying the peroneal nerve and deliver a stimulation signal to it. Contraction of the extensor digitorum brevis (EDB) muscle of the foot, resulting from the stimulation signal, generates a myoelectric potential between the lateral and medial detection sites due to the differential distance between the detection sites and the EDB muscle. The sensing and stimulation electrodes can be selected as described herein for the hand. Any of the multiple stimulation electrodes may be used to monitor the patient. Any of the multiple sensing electrodes can be used to sense the patient response to stimulation. One of the sensing electrodes not being used to sense can be driven to remove common mode signals. Circuitry in the monitor may produce a common mode suppression signal that is applied to the electrode not sensing the muscle activity signal.

Figure 16:
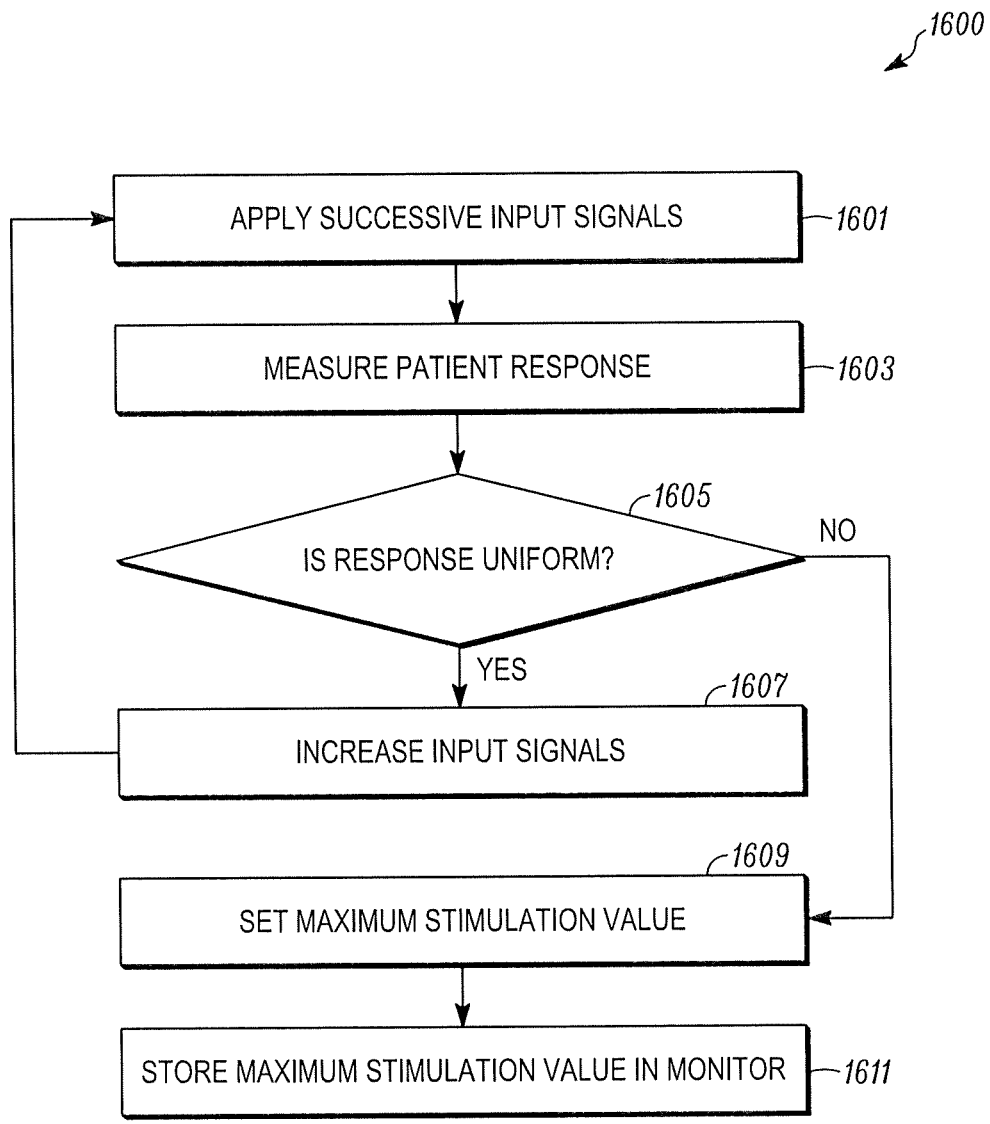
FIG. 16 shows a flow chart showing a neuromuscular monitoring process according to an example embodiment.
Figure 19:
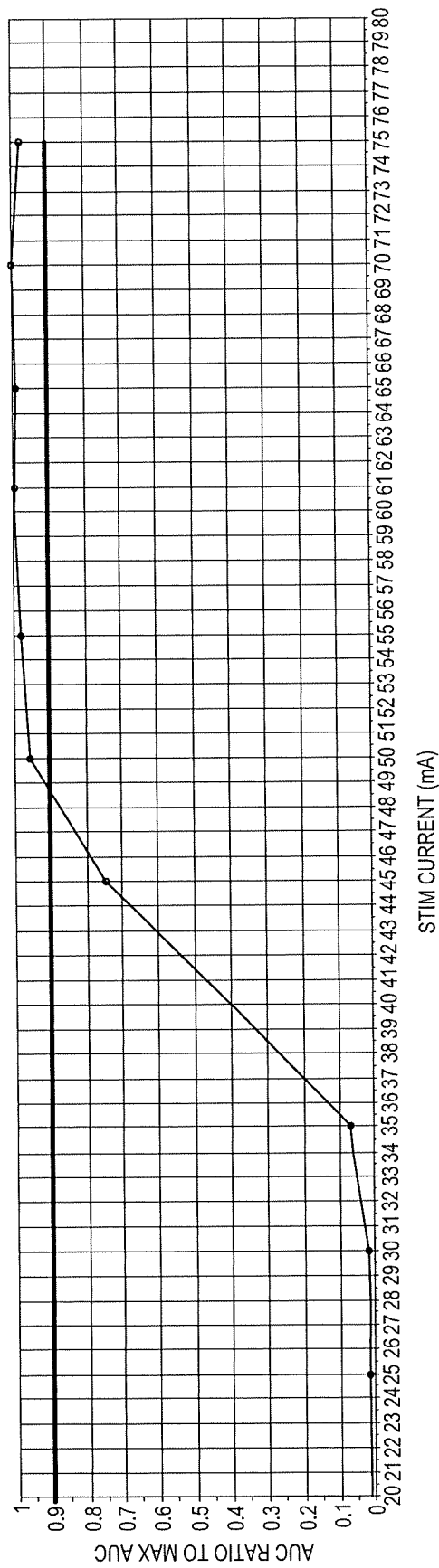
FIG. 19 shows a sample patient response during a calibration process according to an example embodiment.

FIG. 16 shows a method for calibrating the monitor to apply stimulation signals to the patient through the lead assembly. At 1601, the monitor applies successive stimulation signals to the patient through the lead assembly. The first stimulation signal starts at a value that is unlikely to cause a response change in the patient between the successive signals. A sample graph of a response is shown in FIG. 19. In an example, the calibration starts at a 20 milliamps. The stimulation signals can be a set of signal for a train of four (TOF) analysis. When TOF signals are used, then the first response ($T_1$) in successive TOF signals as well as the TOF ratio is used to calibrate the stimulation to the particular patient. At 1603, the patient response to the input signals is measured. At 1605, it is determined if the TOF ratio in response to the input signals was uniform (e.g., within a margin of error) as well as the $T_1$ increased or stayed the same. If the TOF ratio is uniform and the $T_1$ response increased, then at 1607, the value of the input signals is increased. Then the process returns to step 1601. The increase can be an increase described herein, e.g., an increase of 5 milliamps, e.g., 20 to 25 milliamps. If at 1605 the TOF ratio is not uniform, then the process ends. If at 1605 the TOF ratio and the $T_1$ response did not increase, the method proceeds to step 1609. The maximum stimulation value is set using the value of this stimulation signal. A set incremental value, e.g., a factor or a constant, is applied to the value of the successive input signals, e.g., multiplied by a factor or a constant is added, to set the maximum stimulation value. At 1611, the maximum stimulation value is stored in the monitor.

In an example embodiment of calibration, the process will step through multiple stimulation signals between about 10-70 milliamps and look for the stimulation signal that results in a TOF ratio that is constant with no increase in the $T_1$ response. This stimulation value will be used to set the stimulation signal e.g., the supramaximal stimulation signal.

The supramaximal signal for excitation can be set by starting with a start signal, e.g., a single twenty mA stimulus. The value of the excitation signal is increased by an incremental value, e.g., five mA, up to a maximum, e.g., eighty mA. The supramaximal signal is the excitation signal required to activate the maximal number of fibers in the stimulated muscle. Once the calibration sequence is completed, all the calculated amplitudes are normalized to the maximum response. The minimum stimulus amplitude that elicits a response at least 90% of the maximal response is selected, and this current is increased by a value greater than one (e.g., 110%, 120%, 125%) resulting in a supramaximal current setting.

Figure 17:
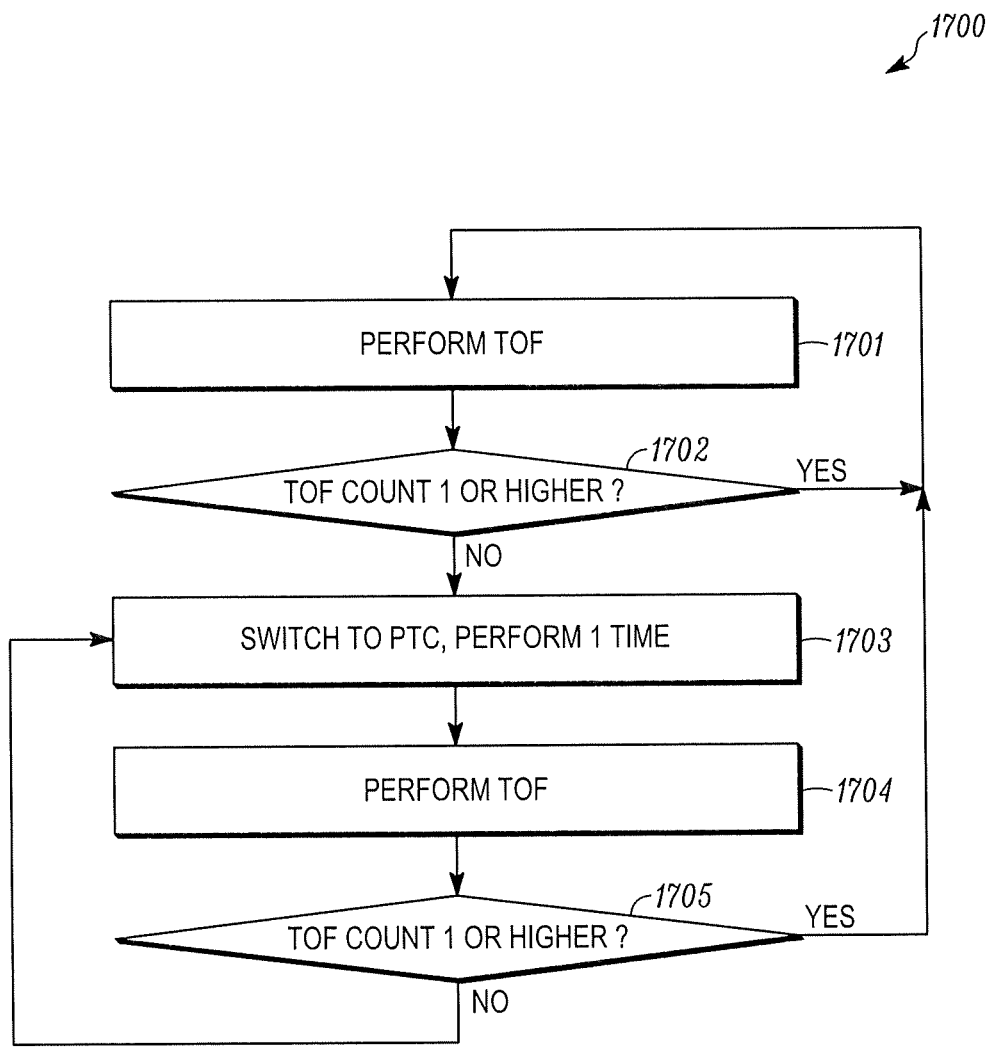
FIG. 17 shows a flow chart showing a neuromuscular monitoring process according to an example embodiment.

FIG. 17 shows a method 1700 that can be performed by the monitor to automatically switch between monitoring light to medium block and monitoring deep neuromuscular block. If the patient is significantly paralyzed (TOF count=0), a more sensitive sequence (post tetanic count, PTC) can be used to quantify deep paralysis. The monitor will detect TOF count=0, and switch automatically to PTC monitoring. If significant neuromuscular recovery occurs (TOF count of 1 or more on standard TOF), the monitor will switch back to TOF monitoring and discontinue PTC measurements. For PTC measurements, a stimulation signal at the supramaximal stimulation value is applied at 50 Hz for about five seconds. At 1701, the TOF analysis is performed. At 1702 if the TOF count is one or higher, then the method can continue to perform TOF analysis, e.g., by returning to step 1701. If at 1702, the TOF count is less than one, then the method switches to a post tetanic count (PTC) at 1703. The PTC 1703 is performed once. At 1704, the TOF analysis is again performed. At 1705, if the TOF count is one or higher the method returns to step 1701. If the TOF count is not one or higher, then the method returns to step 1703 and performed the PTC.

Figure 18:
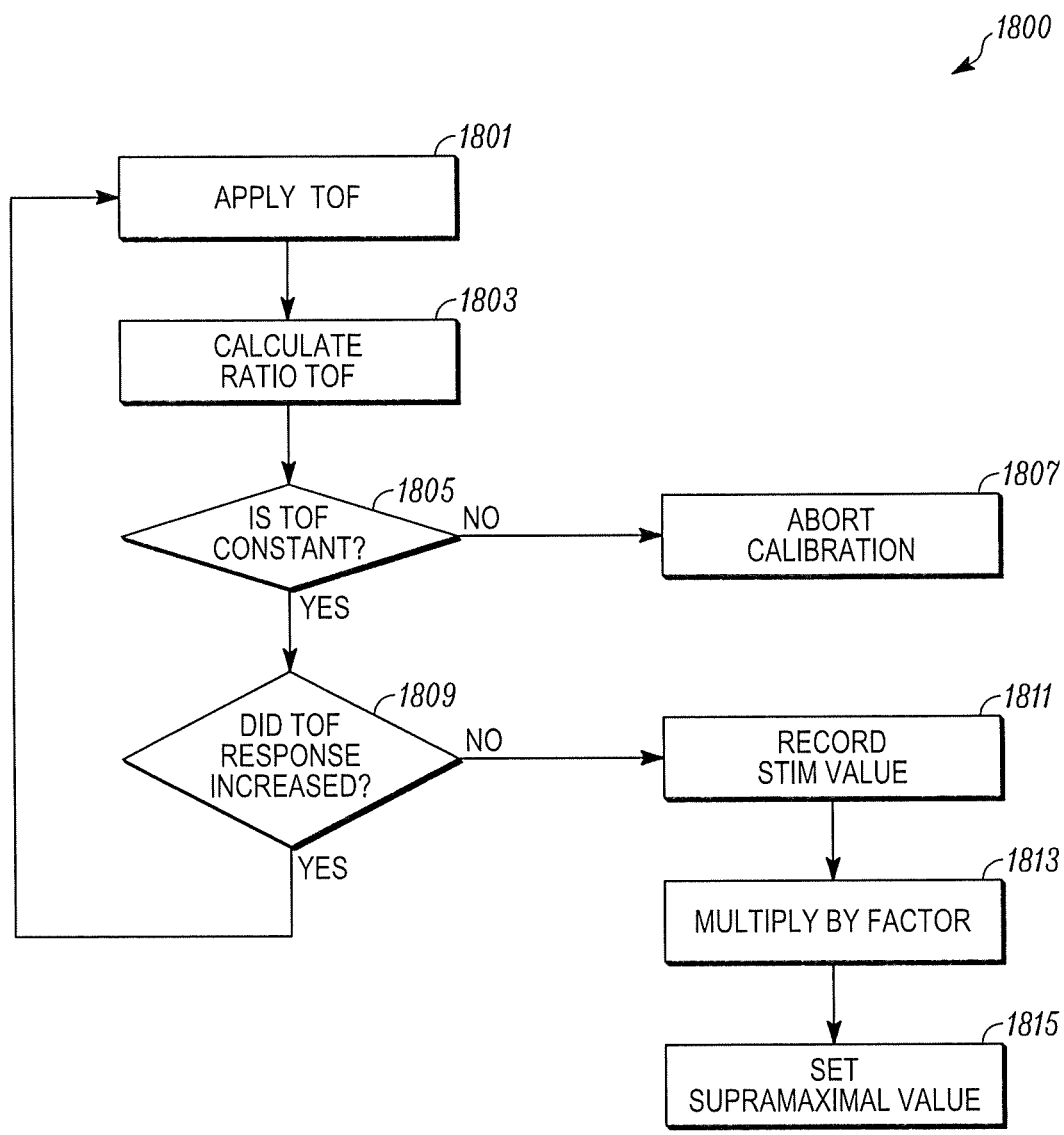
FIG. 18 shows a flow chart showing a neuromuscular monitoring process according to an example embodiment.

FIG. 18 shows an example embodiment of calibrating stimulation signals 1800. At 1801, a TOF is applied to the patient through the selected electrode of the lead. The TOF is performed at a first stimulation signal value. At 1803, the TOF ratio is determined. At 1805, if the TOF ratio is not constant with the prior TOF ratio, then the calibration is aborted at 1807. At 1807, the value of the TOF signals stored in memory in the calibration 1800 is reset. After a time period, e.g., a few minutes or ten minutes, the calibration method may be restarted from the beginning. If the TOF is constant, the calibration moves to step 1809. At 1809, if the $T_1$ response in the TOF increases, then the maximum stimulation signal has not been reached and the calibration 1800 returns to step 1801 and increases the stimulation signal by an incremental value, e.g., 20%, 5 milliamps, 3 milliamps, 2.5 milliamps, or 10 milliamps. When the $T_1$ response in the TOF does not increase, then the maximum stimulation signal was reached. At 1811, the stimulation signal value is recorded, e.g., the amps used in the signal. At 1813 the stimulation signal value is increased by a factor to determine a supramaximal stimulation signal. The factor can be a constant (e.g., 2.5 milliamps, 3, milliamps, 5, milliamps, +/0.05 milliamps, or the like) or an arithmetic factor, e.g., 1.05 1.1, 1.2. 1.25. At 1815 the supramaximal stimulation signal is set and stored in the monitor. The supramaximal stimulation signal is used to detect the state of the patient, TOF analysis and detection, during the medical procedure.

At 1807 the calibration is aborted. The calibration may be restarted after a waiting time period. The waiting time period may be two minutes, five minutes, ten minutes or fifteen minutes. The calibration method may also have a limit on the number of times that calibration is performed. This limit may be part of step 1807 and stops future calibration attempts once the limit is reached.

FIG. 19 shows a graph of a response to a stimulation current applied to a patient. In an example embodiment, this curve shows the stimulation signal used to calibrate the stimulation signal for use in neuromuscular blockade monitoring. The calibration stimulation signal may start at a minimum value, e.g., 15 mA, 20 mA or 25 mA. The calibration signal may be incremented by an incremental value, e.g., 1 mA, 2.5 mA, 5 mA or the like. The calibration signal may also end at a maximum value, e.g., 60 mA, 65 mA, 70 mA, 75 mA, 80 mA, 85 mA, or 90 mA. The range of calibration signal is such that it should determine the stimulation signal required to achieve accurate TOF responses in a majority of patients. Calibrating the stimulation signal over range of stimulation values allows the present method and system to account for some anomalies in the data.

The y-axis in FIG. 19 represents the EMG amplitude (calculated using an area under the curve of the raw EMG signal) divided by the maximum EMG amplitude. The maximum EMG amplitude is determined after applying all the stimulation signals (e.g. all the stimulation signals from 20 mA to 75 mA as in the example if FIG. 19). The stimulation value to use in at 1811 may be selected as the lowest stimulation amplitude that exceeds a ratio of 0.9 in FIG. 19 (90% of the maximum EMG signal). In the example in FIG. 19, this stimulation value would be selected as 50 mA.

Figure 20:
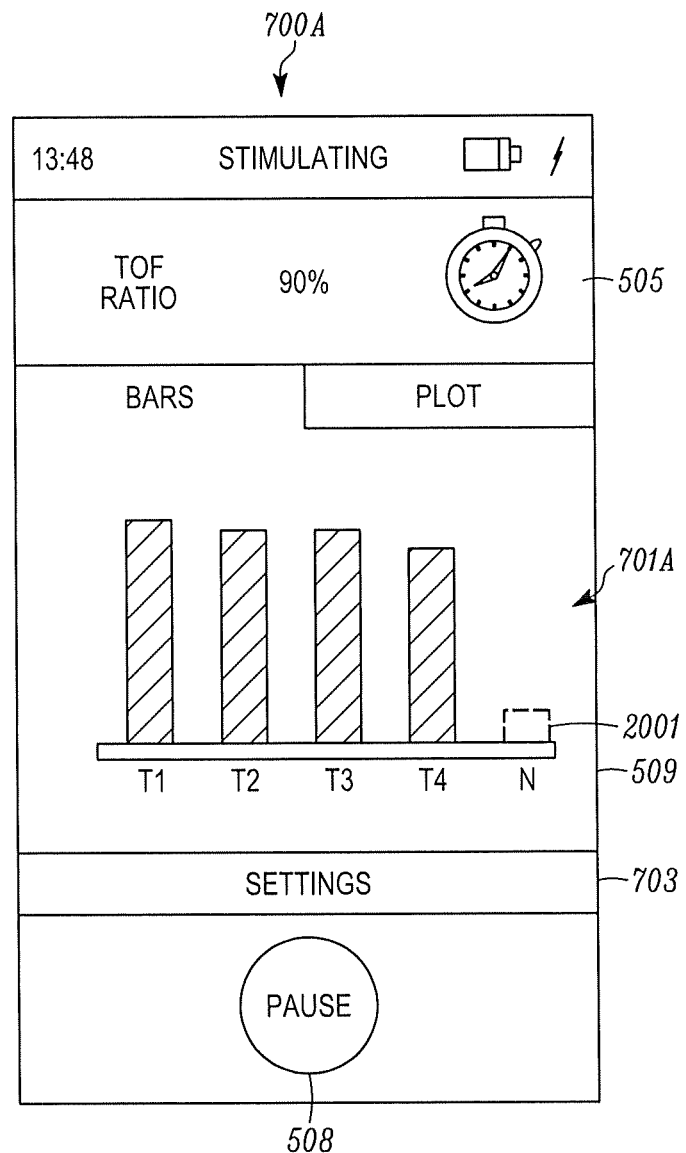
FIG. 20 shows a schematic view of a control unit for a neuromuscular monitoring system, during a process step, according to an example embodiment.

FIG. 20 shows a graphical user interface 700A, which is similar to the interface 700 described herein and shown on a display that is part of the monitor 101. Interface 700 is at a stimulation stage, which is at a further stage of operation relative to interfaces 500 and 600. The first display area 505 shows the reading of TOF ratio, here as 90%. The third display area 509 shows the train of four results as a bar graph 701, with each bar being a reading at times T1, T2, T3 and T4. The third display area 509 shows a further testing result 2001, which represents a noise test N. The noise test N can be the result of sensing the patient response when no stimulation signal is applied to the patient. In an example, the time period for the noise test N is the same as at least one of the reading times T1, T2, T3 and T4. In an example the time for noise test N and the reading times T1, T2, T3 and T4 are all the same length of times. In operation, the present system and methods may subtract the sensed noise from the results shown at the reading times T1, T2, T3 and T4. The noise may be from the electromagnetic emissions with the environment, e.g., an operating room, or from the circuitry of the device itself. By sensing the noise, the present system may use this sensed value to account for noise and provide more accurate readings in the TOF readings and results. The settings icon 703 is provided to allow the user to return the process back to the settings stage as shown in FIG. 6, which can also set the duration of the noise sensing. The control button 508 is now a pause button to stop the stimulation and reading of the results by the monitor 101.

The y-axis in FIG. 19 represents the EMG amplitude (calculated using an area under the curve of the raw EMG signal) divided by the maximum EMG amplitude. The maximum EMG amplitude is determined after applying all the stimulation signals (e.g. all the stimulation signals from 20 mA to 75 mA as in the example of FIG. 19). The stimulation value to use in at 1811 may be selected as the lowest stimulation amplitude that exceeds a ratio of 0.9 in FIG. 19 (90% of the maximum EMG signal). In the example in FIG. 1 9, this stimulation value would be selected as 50 mA.

FIG. 20 shows a graphical user interface 700A, which is similar to the interface 700 described herein and shown on a display that is part of the monitor 101. Interface 700 is at a stimulation stage, which is at a further stage of operation relative to interfaces 500 and 600. The first display area 505 shows the reading of TOF ratio, here as 90%. The third display area 509 shows the train of four results as a bar graph 701, with each bar being a reading at times T1, T2, T3 and T4. The third display area 509 shows a further testing result 2001, which represents a noise test N. The noise test N can be the result of sensing the patient response when no stimulation signal is applied to the patient. In an example, the time period for the noise test N is the same as at least one of the reading times T1, T2, T3 and T4. In an example the time for noise test N and the reading times T1, T2, T3 and T4 are all the same length of times. In operation, the present system and methods may subtract the sensed noise from the results shown at the reading times T1, T2 T3 and T4. The noise may be from the electromagnetic emissions with the environment, e.g., an operating room, or from the circuitry of the device itself. By sensing the noise, the present system may use this sensed value to account for noise and provide more accurate readings in the TOF readings and results. The settings icon 703 is provided to allow the user to return the process back to the settings stage as shown in FIG. 6, which can also set the duration of the noise sensing. The control button 508 is now a pause button to stop the stimulation and reading of the results by the monitor 101.

Figure 21:
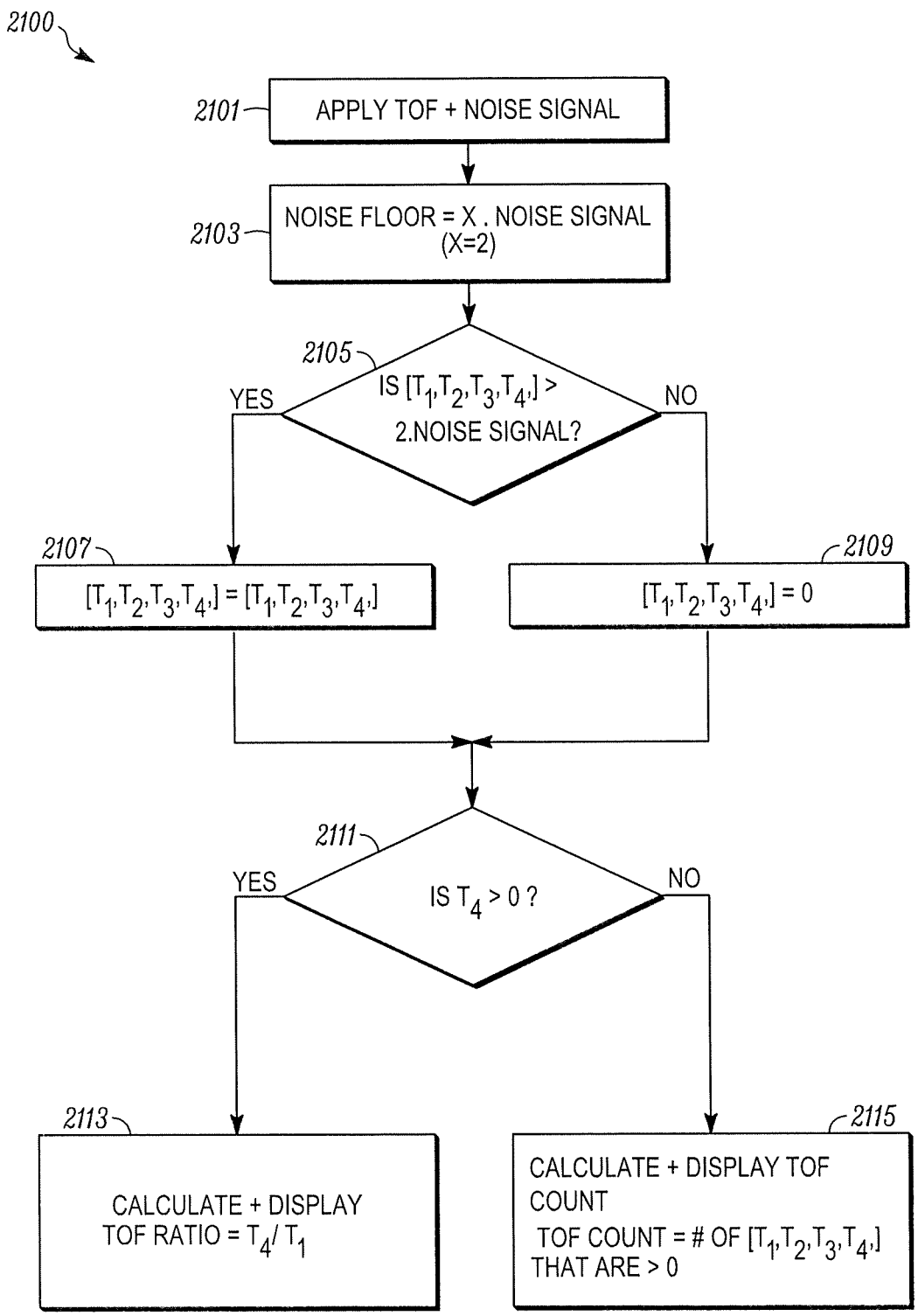
FIG. 21 shows a flow chart showing a neuromuscular monitoring process according to an example embodiment.

FIG. 21 shows an example embodiment for accounting for possible noise in the TOF signals. At 2101, a TOF and a noise signal is applied to the patient through the selected electrode of the lead. The TOF signals may be determined according to any of the teachings herein or using other methods. The noise signal can be determined during a non-stimulation signal time period, e.g., before or after the TOF stimulation signal. The noise component may affect the determination of the status of the patient, which is derived from the train of four signal response. At 2103, a noise floor value is set. The noise floor value can be set to be greater than the noise signal itself. In an example, the noise floor value is set to twice the noise signal. In an example, the noise floor value is a multiple of the noise signal, e.g., X times the noise signal, where X is a real number 2 or greater. In an example, X can be up to 5 or 10. At 2105, it is determined if each of the TOF values sensed at the patient is greater than the noise floor value. If each of the TOF sensed values ($T_1$, $T_2$, $T_3$, $T_4$) is greater than the noise floor value, then at 2107 the TOF sensed values are accepted and the process moves to step 2111. If any of the TOF sensed signals ($T_1$, $T_2$, $T_3$, or $T_4$) are less than or equal to the noise floor signal, then at 2109 the TOF sensed signals that are less than or equal to the noise floor signal are set to zero. In an example embodiment, the one or more than one of the TOF sensed signal is less than the noise floor value, then that TOF sensed value is set to zero. Then the process moves to 2111, whereat it is determined if the last sensed TOF signal $T_4$ is greater zero. If the sensed TOF signal $T_4$ is greater than zero, then at 2113 the TOF ratio is calculated and stored. The TOF ratio can also be displayed to the medical professional and used as described herein. If the sensed TOF signal $T_4$ is less than or equal to zero, then at 2115 the TOF count is calculated and stored. The TOF count is the number of sensed TOF values greater than zero. The TOF count can also be displayed to the medical professional and used as described herein.

Figure 22:
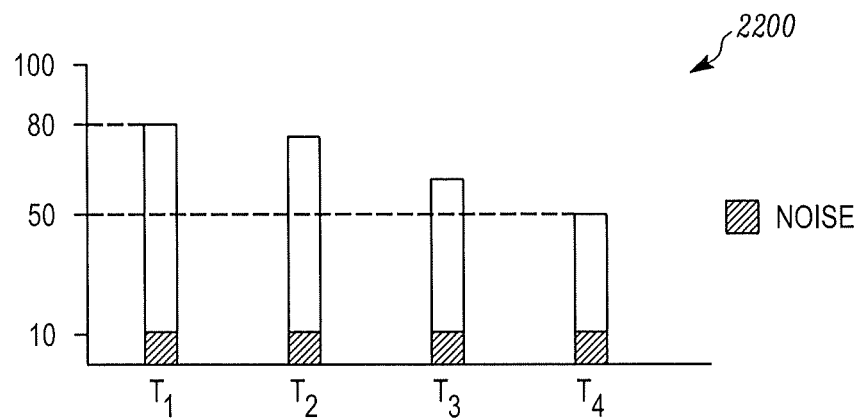
FIGS. 22-24 show graphs of Train-Of-Four signals resulting from the methods and systems described herein to example embodiments.
Figure 23:
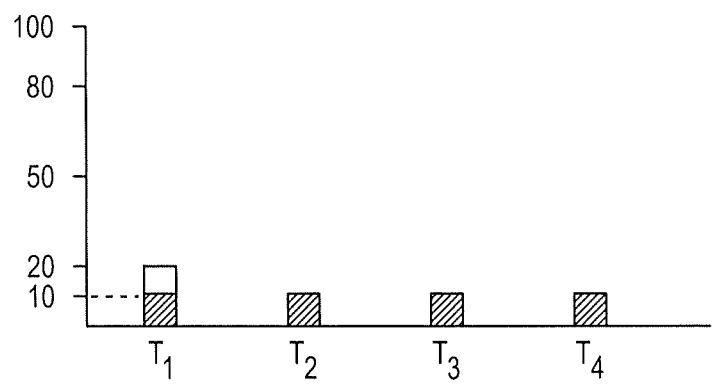
Figure 24:
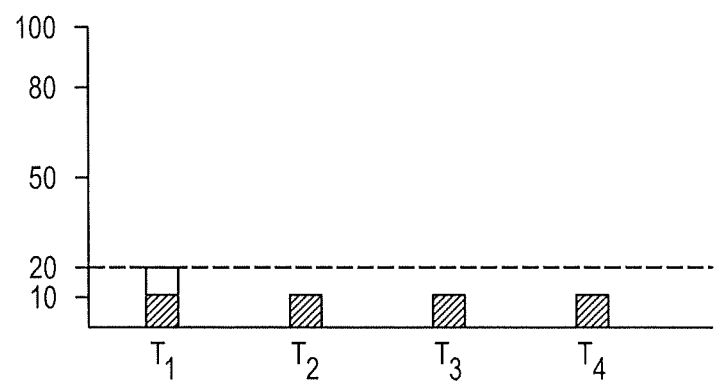

FIGS. 22-24 show graphs of TOF responses to a stimulation current applied to a patient. The noise portion of the sensed TOF signals is shown in the hashed portions of sensed signals. The noise value can be sensed at any time range not in the time periods of $T_1$, $T_2$, $T_3$, or $T_4$. As shown in FIG. 22, the graph 2200, a constant noise value of about 10, which is about 10% of the maximum value. Here the TOF ratio ($T_4/T_1$) is about 62.5% (50/80). The values of the TOF sensed values all exceed the noise. This will result in an accurate TOF ratio.

FIG. 23 shows the TOF values noise at each of the TOF values ($T_1$, $T_2$, $T_3$, or $T_4$) is sensed. The first sensed value $T_1$ is 20. The other values $T_2$, $T_3$, $T_4$ are equal to the noise value. Hence, each of $T_2$, $T_3$, and $T_4$ should all be zero as the sensed value as a result of the stimulation signal is actually zero or negligible in view of the noise. The sensed value of $T_1$ is 20. The sensed value of $T_4$ is 10, which is the noise sensed at the patient. Using these values results in a traditional TOF ratio calculation results in a TOF value (ratio) of 50% (10/20). However, this is an erroneous result, the actual value (i.e., the value without the noise) is zero. Thus, the corrected TOF ratio as produced by the present system and methods is zero when corrected for the noise value. Embodiments of the present invention set a noise floor value. When the signals do not exceed the noise floor value, then the system will not calculate the values, e.g., TOF ratios, other sedation indicators based on the sensed signals or the like using the sensed signal(s).

FIG. 24 shows the same results as FIG. 23 with the noise floor value being set at an amount greater than the noise value, here, greater than 10 millivolts. Here the noise floor is set to 20 millivolts. In some examples, the noise floor can be an actual sensed noise value or the actual sensed noise value plus a small factor added thereto. In the present example as shown in FIG. 24, the correct TOF ratio is now correctly computed to zero. The TOF count is one. The $T_1$ value is the only value that is at least at the noise floor value or more than the noise floor value.

While some embodiments have the noise sensing after the sensing of the TOF results at T1, T2, T3 and T4 the present description is not so limited. The noise sensing may occur before the TOF sensing, i.e., before T1. The noise sensing may occur intermediate any of the TOF sensing, i.e. intermediate T1 and before T4, intermediate, T1 and T2 or intermediate T3 and T4. When sensing the noise, the stimulation signal (e.g., the current) is set to zero. The sensed noise signal can be used as a floor below which the present system will not compute TOF values. The TOF values are not calculated when a sensed signal is equal to or less than the noise signal value to reduce the likelihood of erroneous calculations. In an example embodiment, the noise signal value is the sensed value plus a safety margin added thereto, e.g., 2.5%, 5%, 7%, 10%, or the like added thereto. In some examples, different safety values can be used for the TOF results T1, T2, T3, and T4. For example, the safety margin for T1 can be greater than the safety margin for T2, T3, or T4.

In an example embodiment, the sensed noise value can be used to set the stimulation current, e.g., the beginning signal to determine the stimulation signal value. The sensed noise signal may be 5.0 millivolts. Thus, the stimulation current for the TOF procedure is set so the resulting EMG signal is at least 10 millivolts to have a signal-to-noise ratio of at least 2.0.

The present methods and systems that account for noise can sense noise from various sources, e.g., common mode noise, 60 Hz common mode, stray electromagnetic signals from the power source or from another device in the operating room, which may or may not be connected to the patient. The sensing of noise can be thought of as adding a fifth sensing period to the train-of-four signal scheme. While the TOF system applies a stimulation signal and senses a response during a time period subsequent to the start of the stimulation signal, this fifth sensing period may be sensed without a stimulation signal. The fifth sensing period is spaced in time from any of the stimulation signals. The present description allows the noise to be measured in real-time during the medical procedure and may increase accuracy for an individual and the individual operating room. The present system will not calculate a TOF value if the sensed values fall at or below the noise floor value.

In an example embodiment, a factor or constant can be used to increase the stimulation signal to set signal-to-noise floor or signal-to-noise ratio. Such a signal to noise ratio may be greater than 1.4 and up to 2.5 or 3.0 or 4.0. The signal to noise ratio may be set in the range of about 1.5 to 4.0 or in a range of 1.6 to 3.0 or 4.0, +/−0.1. In some examples, the signal to noise ratio is set to 2.5.

The train of four monitoring can be repeating test sequences, with a pause between the train of four stimulation pulses. This allows the system to sense the noise value and allows the patient's body to recover from the prior train of four pulses. In an example, the sequence of train of four patient measurement occurs every 12-15 seconds, every 20 seconds, or every 30 seconds.

The presently described systems and methods, when the TOF patient monitoring may not be producing reliable results, e.g., when the sensed signals do not exceed the noise floor threshold value, can switch to other patient monitoring schemes. Examples of other patient monitoring can include post-tetanic count, single twitch or tetanus sensing. If the TOF count drops to zero, the system will prompt the user to switch to post tetanic count (PTC) to monitor deep neuromuscular blockade. If selected, PTC is then repeated every ten minutes as long as the patient continues to be in deep neuromuscular blockade (e.g., defined as a TOF Count of zero). If the TOF count recovers to 1 or higher, the system switches back to TOF stimulation. Thus, the present systems and methods can provide for one or more than one patient monitoring schemes, which can be based, at least in part, on the TOF sensed patient response.

The PTC stimulation sequence by the present system is used to monitor deep neuromuscular blockade and may include of a five second, fifty Hz tetanic stimulation (to make the muscle more responsive) followed by a three second pause and then a series of single stimuli (up to 15 total) delivered once per second. The number of detectable responses to the single stimuli is counted and reported as the post tetanic count. The fewer the detected responses, the deeper the neuromuscular blockade. To ensure PTC is only used in patients with deep neuromuscular blockade, a TOF is performed at the beginning of each PTC stimulation sequence. The tetanic stimulation is only delivered if the TOF count is zero (no detectable twitches in the patient). Additional tetanic stimuli are prohibited for about two minutes following the last tetanic stimulation. The progress of the PTC stimulation sequence can be displayed dynamically during stimulation. The PTC stimulation can be repeated between five minutes and ninety minutes.

A single twitch response may include a single stimulation pulse delivered to the patient and then the EMG response is measured and displayed. If the system has been calibrated, the calibration twitch height will be shown on the display and all subsequent single twitches will be scaled to the calibration value (0-100%). If calibration has not been performed, the response height is displayed on a fixed scale (0-100). The single twitch process can be repeated every ten seconds to sixty minutes.

The system can deliver a five-second, fifty Hz tetanic stimulation. During tetanic stimulation. EMG sensing is not active. Additional tetanic stimuli are prohibited for two minutes following the last tetanic stimulation. Likewise, TOF sensing is delayed after tetanic stimulation. Typically, the present system does not set a repeat for tetanic stimulation.

The present disclosure also includes using the determination of the maximum or supramaximal stimulation signal as part of the determination of the sensing electrode. In this process, each sensing electrode (e.g., at least two different electrodes, e.g., 303, 404) is used in the process to determine the supramaximal signal. The other of the electrode may be the driven electrode to eliminate common mode signals. The results of the supramaximal determinations for each electrode can be used to select which electrode will be used to sense the response to a stimulation signal. In some example embodiments, the sensed noise may be used to set the minimal value for the stimulation signal.

The circuitry in the monitor to detect and suppress the common mode signal may include a right-leg drive amplifier.

The present description described surface electrodes that are adhered to the skin of a patient. The electrodes can be adhered with adhesive, e.g., adhesive that surrounds the electrically conductive part of the electrode. In an example, surgical tape may be used to fix the electrodes to the patient's skin. It will be within the scope of the present disclosure to also include needle electrodes that penetrate the patient's skin. It may be useful to use needle electrodes when a patient has thick, dry skin, e.g., calluses, scar tissue, abnormally thick skin, or the like, at the electrode locations.

The present description uses phrases like "electrical communication," "communication" and terms of similar import. Such communication may be wireless, wired, or through a biological connection, e.g., through a body of a person.

The quantitative neuromuscular blockade monitoring (sometimes referred to as "twitch" monitoring) as described herein may provide improved patient care and satisfaction and may reduce the incidence of respiratory complications.

The quantitative neuromuscular blockade monitoring can be used with general anesthetic and is not limited to local anesthetic.

The present disclosure may be used in conjunction with the drug Sugammadex, currently supplied by Merck. Sugammadex is a fast acting drug that reverses neuromuscular blockade, for example after administration of non-depolarizing neuromuscular-blocking agents such as vecuronium or rocuronium. The drug is approved for use in the European Union, Japan, and Australia. Sugammadex is currently under review by the FDA in the United States. While popular, Sugammadex is quite expensive and its dosing instructions require the use of neuromuscular monitoring.

Outpatient surgery does not require an overnight hospital stay. One purpose of outpatient surgery is to keep hospital costs down, as well as saving the patient time that would otherwise be spent in the hospital. Outpatient surgery has grown in popularity due to the rise in outpatient surgery centers and improved technology and now accounts for about 65% of all surgical procedures. One emphasis of outpatient surgical centers is a safe and speedy surgical recovery time, which may be facilitated by rapid reversal of anesthesia once the surgical procedure is completed. Specifically, the use of the anesthesia recovery drugs, e.g., a combination of rocuronium and Sugammadex, may require careful objective monitoring of neuromuscular blockade results in a rapid recovery of from neuromuscular blockade will reducing the risk of a dangerous partial neuromuscular blockade and the related morbidity and mortality.

The present disclosure can establish a noise floor value that represents noise or an ambient sensed signal that is below a value of a response in a patient that has been administered a neuromuscular blockade drug. The sensed signal must be above this noise floor value for the system to use the sensed data to compute the status of the patient. The train of four calculations will not be performed or will not be output from the device, i.e., not provided to the medical professional, with the sensed signal being below the noise floor. This will reduce the likelihood of an erroneous output from the system being provided to the medical professional.

The present disclosure provides systems and methods for medical professionals, e.g., anesthesiologists, to monitor the depth of neuromuscular blockade objectively. In the past, a subjective test was performed, which may result in extubation of the patient before full reversal of the neuromuscular blockade. It has been reported that premature extubation may occur in about 2% of surgeries, i.e., the patient wakes up partially paralyzed.

The present disclosure further addresses problems with other prior methods or devices. The present lead assembly may include a thumb aperture to assist in properly positioning electrodes. At most there are only two bases, and in an example embodiment, a single unitary base, with electrodes that need to be secured to skin as opposed to individual electrodes in the prior devices. The presently described electrodes are all on a single, unitary base or two bases, each with at least two electrodes. The cables for electrical communication to the electrodes are supported by the base. A unitary, single-bodied connector can connect the multiple conductors to the monitor. This reduces the risk of tangling multiple wires or connecting the wrong cable to the wrong electrode. The conductors are integral and will not pull off the electrodes. The present lead assembly can be made as a single use device. The present lead assembly may reduce setup time, reduce placement errors, and failure during ongoing operation, either due to a wires breaking or the wires being inadvertently pulled off the pads.

It will be recognized that any one of the claims can be combined with each other. The claims are presented as singly dependent but can be combined with each other in any combination.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A neuromuscular lead assembly, comprising:
a base;
a monitor including a processor;
a plurality of stimulation electrodes mechanically supported by the base and configured to be connected to a patient;
a plurality of sensing electrodes supported by the base and in electrical communication with the patient, the plurality of sensing electrodes being configured to electrically communicate with a processor to detect muscle activity in response to a stimulation from at least one of the plurality of stimulation electrodes; and
wherein the monitor includes a modality of selection functionality such that the plurality of sensing electrodes is configured selectable by the monitor with at least a first one of the plurality of sensing electrodes selected by the monitor as a detection electrode and at least a second one of the plurality of sensing electrodes selected by the monitor as a driven electrode;
wherein the detection electrode is configured for detecting a common mode signal that is indicative of ambient noise from the patient, and the common mode signal is not in response to the stimulation from the at least one of the plurality of stimulation electrodes, the monitor is configured to suppress the common mode signal detected by the detection electrode by inverting the common mode signal to generate a common mode suppression signal;
wherein the second one of the plurality of sensing electrodes is selected as the driven electrode by the monitor based on an analysis of the muscle activity detected by the second one of the plurality of sensing electrodes indicating non-optimal detection relative to the plurality of remaining sensing electrodes, the non-optimal detection including the sensed signal detected by the second one of the plurality of sensing electrodes not indicating a maximal signal height.

2. The lead assembly of claim 1, wherein the sensing electrodes sense an electrical noise floor, and the monitor is configured to set a minimum sensed signal to be greater than the electrical noise floor and to use sensed signals from the plurality of sensing electrodes that are greater than the electrical noise floor value in a train-of-four calculation.

3. The lead assembly of claim 1, wherein the base is nonlinear to position the plurality of sensing electrodes at anatomically desired positions on a hand of the patient and the plurality of stimulation electrodes at anatomically desired positions on a forearm of the patient.

4. The lead assembly of claim 1, wherein the first one of the plurality of sensing electrodes is selected as the detection electrode by the monitor based on an analysis of the muscle activity detected by the first one of the plurality of sensing electrodes indicative of optimal detection relative to the plurality of remaining sensing electrodes, the optimal detection including a sensed signal detected by the first one of the plurality of sensing electrodes indicating a maximal signal height.

5. The lead assembly of claim 1, wherein the base, the plurality of stimulation electrodes and the plurality of sensing electrodes are disposable.

6. The lead assembly of claim 1, wherein the base includes medical grade adhesive to fix the plurality of sensing electrodes to the patient for sensing electrical activity.

7. The lead assembly of claim 1, wherein the base includes a thumb aperture to secure the base around a thumb of the patient to position a first sensing electrode on a palm of the patient and a second sensing electrode on a back of a hand of the patient.

8. The lead assembly of claim 1, wherein the monitor is configured to drive the stimulation signal to the driven electrode and to sense the ambient noise with the detection electrode of the plurality of sensing electrodes.

9. The lead assembly of claim 8, wherein the monitor is configured to set the stimulation signal to be greater than a noise floor, and the plurality of sensing electrodes senses a sensed signal that must be greater than the noise floor value to be used in the train-of-four calculation.

10. The lead assembly of claim 1, wherein each of the plurality of sensing electrodes includes microneedles to penetrate the surface of a stratum corneum layer.

11. The lead assembly of claim 1, wherein the driven electrode is configured for applying the common mode suppression signal to a sensed signal detected by one or more of the plurality of sensing electrodes in response to the stimulation from the at least one of the plurality of stimulation electrodes, such that the ambient noise from the patient is removed from the sensed signal.

12. The lead assembly of claim 1, wherein the monitor is configured to conduct quantitative twitch monitoring by applying a plurality of discrete stimulation pulses via one or more of the plurality of stimulation electrodes and sensing a response from the patient to each of the plurality of stimulation pulses via one or more of the plurality of sensing electrodes.

13. The lead assembly of claim 1, wherein the monitor is configured to conduct a calibration routine that gradually raises a stimulation current applied to the patient from the plurality of stimulation electrodes until the monitor determines that further increases in the stimulation current do not elicit a larger muscle twitch response from the patient.

14. A neuromuscular lead assembly, comprising:
a body;
a monitor including a processor;
a plurality of electrodes mechanically supported by the body;
an accelerometer;
a plurality of conductors supported by the body and in electrical communication with the plurality of electrodes; and
wherein the plurality of conductors and the accelerometer are configured to electrically communicate with the processor to detect muscle movement from a patient in response to stimulation delivered to the patient by at least one of the plurality of electrodes;
wherein the monitor includes a modality selection functionality, such that the plurality of electrodes include at least one electrode selected by the monitor as a detection electrode for sensing an ambient electrical signal at the body when the at least one electrode is not selected by the monitor to apply a stimulation signal or sense the patient response to the stimulation signal, wherein the monitor is configured to suppress the ambient electrical signal sensed by the detection electrode by inverting the ambient electrical signal into a suppression signal;
wherein the plurality of electrodes includes at least one electrode selected by the monitor as a driven electrode for applying the suppression signal to a sensed signal detected by one or more of the plurality of electrodes from the patient response to the stimulation signal;
wherein the at least one electrode selected as the driven electrode by the monitor is based on an analysis of the muscle movement detected by the driven electrode indicating non-optimal detection relative to the plurality of remaining electrodes, the non-optimal detection includes the sensed signal detected by the driven electrode not indicating a maximal signal height.

15. The lead assembly of claim 14, wherein the plurality of electrodes include a stimulation electrode configured to apply the stimulation signal to the patient.

16. The lead assembly of claim 15, wherein the plurality of electrodes includes a sensing electrode to sense the patient response to the stimulation signal applied by the stimulation electrode.

17. The lead assembly of claim 15, wherein the plurality of electrodes includes more than one sensing electrode configured to sense the patient response to the stimulation signal applied by the stimulation electrode.

18. The lead assembly of claim 14, wherein the monitor is configured to conduct quantitative twitch monitoring by applying a plurality of discrete stimulation pulses via one or more of the plurality of electrodes and sensing a response from the patient to each of the plurality of stimulation pulses via one or more of the plurality of electrodes.

19. The lead assembly of claim 14, wherein the monitor is configured to conduct a calibration routine that gradually raises a stimulation current applied to the patient from the plurality of electrodes until the monitor determines that further increases in the stimulation current do not elicit a larger muscle twitch response from the patient.

20. A neuromuscular lead assembly, comprising:
a body;
a monitor including a processor;
a plurality of electrodes on the body; and
a plurality of conductors on the body and in electrical communication with the plurality of electrodes;
wherein the plurality of conductors are configured to electrically communicate with the processor to detect muscle movement from a patient in response to stimulation from at least one of the plurality of electrodes;
wherein the monitor is configured to select at least one of the plurality of electrodes as a detection electrode for sensing an ambient electrical signal in response to the monitor not selecting the at least one electrode to apply a stimulation signal or sense a patient response to the stimulation signal, the monitor is configured to suppress the ambient electrical signal sensed by the detection electrode by inverting the ambient electrical signal into a suppression signal;
wherein the monitor is configured to select at least one of the plurality of electrodes as a driven electrode for applying the suppression signal to a sensed signal detected by one or more of the plurality of electrodes from the patient response to the stimulation signal;
wherein the at least one electrode selected as the driven electrode by the monitor is based on an analysis of the muscle movement detected by the driven electrode indicating non-optimal detection relative to the plurality of remaining electrodes, the non-optimal detection includes the sensed signal detected by the driven electrode not indicating a maximal signal height.

21. The lead assembly of claim 20, wherein the plurality of electrodes includes at least one stimulation electrode configured to apply the stimulation signal to the patient.

22. The lead assembly of claim 20, wherein the monitor is configured to conduct quantitative twitch monitoring by applying a plurality of discrete stimulation pulses via one or more of the plurality of electrodes and sensing a response from the patient to each of the plurality of stimulation pulses via one or more of the plurality of electrodes.

23. The lead assembly of claim 20, wherein the monitor is configured to conduct a calibration routine that gradually raises a stimulation current applied to the patient from the plurality of electrodes until the monitor determines that further increases in the stimulation current do not elicit a larger muscle twitch response from the patient.

24. The lead assembly of claim 20, wherein one or more of the plurality of electrodes are configured to sense an electrical noise floor, and the monitor is configured to set a minimum sensed signal to be greater than the electrical noise floor and to use sensed signals from the one or more of the plurality of electrodes that are greater than the noise floor value in a train-of-four calculation.

\* \* \* \* \*